US008409827B2

(12) United States Patent
Stewart et al.

(10) Patent No.: US 8,409,827 B2
(45) Date of Patent: Apr. 2, 2013

(54) NITRATE REDUCTASE FUSION PROTEINS AND USES THEREOF

(75) Inventors: Jennifer J. Stewart, Milton, DE (US); Kathryn J. Coyne, Milford, DE (US)

(73) Assignee: University of Delaware, Newark, DE (US)

(*) Notice: Subject to any disclaimer, the term of this patent is extended or adjusted under 35 U.S.C. 154(b) by 0 days.

(21) Appl. No.: 13/184,037

(22) Filed: Jul. 15, 2011

(65) Prior Publication Data

US 2012/0034668 A1 Feb. 9, 2012

Related U.S. Application Data

(60) Provisional application No. 61/364,583, filed on Jul. 15, 2010.

(51) Int. Cl.
*C12P 21/04* (2006.01)
*C12N 9/00* (2006.01)
(52) U.S. Cl. ..................................... 435/69.7; 435/183
(58) Field of Classification Search .................. None
See application file for complete search history.

(56) References Cited

PUBLICATIONS

Stewart et al. "Analysis of raphidophyte assimilatory nitrate reductase reveals unique domain architecture incorporating a 2/2 hemoglobin", Plant Mol Biol (2011) 77:565-575.*
Molecular Cloning: A Laboratory Manual—Description : < http://cshlpress.org/default.tpl?action=full&--eqskudatarq=934 > — downloaded Sep. 4, 2012.*
Guillard RRL (1975) In: Smith WL, Chantey MH (eds) Culture of Marine Invertebrate Animals, Plenum Press, New York, pp. 26-60.
Altschul SF et al. (1997) Gapped BLAST and PSI-BLAST: a new generation of protein database search programs. Nucleic Acids Res 25:3389-402.
Armbrust EV et al. (2004) The genome of the diatom *Thalassiosira pseudonana*: ecology, 420 evolution, and metabolism. Science 306:79-86.
Arnold et al. (2006) Bioinformatics 22(2):195-210.
Berges J (1997) Miniview: Algal nitrate reductases. Eur J Phycol 32:3-8.
Bonamore A et al. (2007) A novel chimera: the "truncated hemoglobin-antibiotic monooxygenase" from *Streptomyces avermitilis*. Gene 398:52-61.
Bowler C et al. (2008) The *Phaeodactylum* genome reveals the evolutionary history of 425 diatom genomes. Nature 456:239-44.
Campbell WH (1999) Nitrate reductase structure, function and regulation: Bridging the gap between biochemistry and physiology. Annu Rev Plant Physiol Plant Mol Biol 50:277-303.
Campbell WH (2001) Structure and function of eukaryotic NAD(P)H:nitrate reductase. Cell Mol Life Sci 58:194-204.
Chenna R (2003) Multiple sequence alignment with the Clustal series of programs. Nucleic Acids Res 31:3497-3500.
Coyne KJ, et al. (2004) Modified serial analysis of gene expression method for construction of gene expression profiles of microbial eukaryotic species. Appl Environ Microbiol 70:5298-5304.

Coyne KJ and Craig Cary S (2005) Molecular approaches to the investigation of viable dinoflagellate cysts in natural sediments from estuarine environments. J Eukaryot Microbiol 52:90-4.
Coyne, et al. Comparison of nitrate reductase sequence and expression patterns for the harmfulraphidophytes, *Heterosigma akashiwo* and*Chattonella subsalsa*. Fifth Symposium on Harmful Algae in the U.S., Ocean Shores, WA, Nov. 15-19, 2009.
Coyne KJ (2010) Nitrate reductase (NR1) sequence and expression in the harmful alga *Heterosigma akashiwo* (Raphidophyceae). J Phycol 46:135-142.
Doucha et al. (2005) Utilization of flue gas for cultivation of microalgae (*Chlorella* sp.) in an outdoor open thin-layer photobioreactor. J. Applied Phycology. 17:403-412.
Douskova et al. (2009) Simultaneous flue gas bioremediation and reduction of microalgal biomass production costs. Applied Microbiology Biotechnology. 82:179-185.
Eckardt NA (2005) Moco Mojo: Crystal structure reveals essential features of eukaryotic assimilatory nitrate reduction. Plant Cell 17:1029-1031.
Felsenstein J (1985) Confidence limits on phylogenies: An approach using the bootstrap Evolution 39:783-791.
Fredrickson, et al. (2011) "Inter-strain variability in physiology and genetics of *Heterosigma akashiwo* (Rahpidophyceae) from the west coast of North America.", Journal of Phycology 47(1):25-35.
Fuentes-Grunewald et al. (2009) Use of the dinoflagellates *Karlodinium veneficum* as a sustainable source of biodiesel production. J Ind Microbiol Biotechnol 36:1215-1224.
Gardner PR et al. (2000) Nitric-oxide dioxygenase activity and function of flavohemoglobins. Sensitivity to nitric oxide and carbon monoxide inhibition. J Biol Chem 275:31581-7.
Gladwin, M.T. et al., The functional nitrate reductase activity of the Heme-globins. Blood. Oct. 1, 2008, vol. 112, No. 7, pp. 2636-2647.
Grubina, R. et al., Nitrite Reductase Activity of Hemoglobin S (sickle) provides insight into contributions of Heme Redox Potential Versus Ligand Affinity. The Journal of Biological Chemistry. Feb. 8, 2008, vol. 283, No. 6, pp. 3628-3638.
Gardner PR (2005) Nitric oxide dioxygenase function and mechanism of flavohemoglobin, hemoglobin, myoglobin and their associated reductases. J Inorg Biochem 99:247-66.
Guallar, V., et al. (2009). "Ligand migration in the truncated hemoglobin-II from *Mycobacterium tuberculosis*: The role of G8 Tryptophan" *J. Biol. Chem.* 284(5): 3106-3116.
Hammer Ø, et al. (2001) PAST: Paleontological statistics software package 460 for education and data analysis. Palaeontologia Electronica 4:1-9.
Huang, Z. et al., Enzymatic function of Hemoglobin as a Nitrite Reductase that produces NO under Allosteric Control. Journal of Clinical Investigation, Aug. 2005, vol. 115, No. 8, pp. 2099-2107.
Jin et al. (2008) Enhancement of nitric oxide solubility using Fe(II)EDTA and its removal by green alga *Scenedesmus* sp. Biotechnology and Bioprocess Engineering. 13:48-52.
Karplus PA and Bruns CM (1994) Structure-function relations for ferredoxin reductase. J 462 Bioenerg Biomembr 26:89-99.
Kim D (2006) Nitric oxide synthase-like enzyme mediated nitric oxide generation by harmful red tide phytoplankton, *Chattonella marina*. J Plankton Res 28:613-620.
Kim D et al. (2008) Detection of nitric oxide (NO) in marine phytoplankters. J Biosci Bioeng 105:414-7.

(Continued)

*Primary Examiner* — Suzanne M Noakes
(74) *Attorney, Agent, or Firm* — RatnerPrestia

(57) ABSTRACT

The present invention relates to a novel fusion protein comprising a nitrate reductase (NR) and a truncated hemoglobin N (trHbN) domain. The fusion protein may be used for bioremediation of nitric oxide.

20 Claims, 13 Drawing Sheets

PUBLICATIONS

Kumaraswany et al. (2005) Characterization of microbial communities removing nitrogen oxides from the flue gas: the BioDeNOx process. Applied and Environmental Microbiology. 71(10)6345-6352.

Lama A, et al. (2006) Oxygen binding and NO scavenging properties of truncated hemoglobin, HbN, of *Mycobacterium smegmatis*. FEBS Lett 580:4031-4041.

Lama A et al. (2009) Role of pre-A motif in nitric oxide scavenging by truncated hemoglobin, HbN, of *Mycobacterium tuberculosis*. J Biol Chem 284:14457-14468.

Larkin MA et al. (2007) Clustal W and Clustal X version 2.0. Bioinformatics 23:2947-8.

Lecomte JTJ, et al. (2005) Structural divergence and distant relationships in proteins: evolution of the globins. Curr Opin Struct Biol 15:290-301.

Milani M, et al. (2003) Truncated hemoglobins and nitric oxide action. IUBMB Life 55:623-7.

Millett F and Durham B (2004) Kinetics of electron transfer within cytochrome 477 bc1 and between478 cytochrome bc1 and cytochrome c. Photosynth Res 82:1-16.

Moore AD, et al. (2008) Arrangements 480 in the modular evolution of proteins. Trends Biochem Sci 33:444-51.

Lui, F.E. et al., Enhancing Nitrite Reductase activity of Modified Hemoglobin: bis-tetramers and their PEGylated derivatives, Biochemistry, Dec. 22, 2009, vol. 48, No. 50, pp. 11912-11919.

Blood, A.B. et al., Increased Nitrite Reductase Activity of fetal versus adult ovine hemoglobin, American Journal of Physiology Heart and Circulatory Physiology, Feb. 2009, vol. 296, No. 2, pp. H237-H246.

Selvam RA and Sasidharan R (2004) DomIns: A web resource for domain insertions in known 505 protein structures. Nucleic Acids Res 32:D193-195.

Smagghe BJ, et al. (2008) NO dioxygenase activity in hemoglobins is ubiquitous in vitro, but limited by reduction in vivo. PloS One 3:e2039.

Stewart, et al. Expression of nitrate reductase and RUBISCO in response to nitrogen source, temperature and carbon dioxide concentration in *Heterosigma akashiwo*. ASLO 2009 Aquatic Sciences Meeting, Nice, France, Feb. 2009.

Stewart, et al. Novel globin-containing nitrate reductase chimeric sequences found in the raphidophytes, *Heterosigma akashiwo* and *Chattonella subsalsa*. Fifth Symposium on Harmful Algae in the U.S., Ocean Shores, WA, Nov. 15-19, 2009.

Stolz JF and Basu P (2002) Evolution of nitrate reductase: Molecular and structural variations on a common function. Chembiochem 3:198-206.

Tamura K, et al. (2007) MEGA4: Molecular Evolutionary Genetics Analysis (MEGA) software version 4.0. Mol Biol Evol 24:1596-9.

Twiner MJ, et al. (2001) Toxic effects of *Heterosigma akashiwo* do not 513 appear to be mediated by hydrogen peroxide. Limnol Oceanogr 46:1400-1405.

Vardi A, et al. (2008) Diatom genomes come of age. 515 Genome Biol 9:245.

Vinogradov SN et al. (2005) Three globin lineages belonging to two structural classes in genomes from the three kingdoms of life. Proc Natl Acad Sci USA 102:11385-9.

Vinogradov SN and Moens L (2008) Diversity of globin function: enzymatic, transport, storage, and sensing. J Biol Chem 283:8773-7.

Vogel C, et al. (2004) Structure, function and 517 evolution of multidomain proteins. Curr Opin Struct Biol 14:208-16.

Vuletich DA and Lecomte JTJ (2006) A phylogenetic and structural analysis of truncated hemoglobins. J Mol Evol 62:196-210.

Wittenberg J, et al. (2002) Truncated hemoglobins: A new family of hemoglobins widely distributed in bacteria, unicellular eukaryotes, and plants. J Biol Chem 277:871-4.

Workun GJ, et al. (2008) Evolutionary persistence of the 528 molybdopyranopterin-containing sulfite oxidase protein fold. Microbiol Mol Biol Rev 529 72:228-48.

Yeh SR, et al. (2000) A cooperative oxygen binding hemoglobin from *Mycobacterium tuberculosis*. Stabilization of heme ligands by a distal tyrosine residue. J Biol Chem 275:1679-84.

Yoshihara et al. (1996) Biological elimination of nitric oxide and carbon dioxide from flue gas by marine microalga NOA-113 cultivated in a long tubular photobioreactor. Journal of Fermentation and Bioengineering. 82(4) 351-354.

Xing L, et al. (2005) Amperometric detection of nitric oxide with microsensor in the medium of seawater and its applications. Sensors 5:537-545.

Zhou J and Kleinhofs A (1996) Molecular evolution of nitrate reductase genes. J Mol Evol 42:432-42.

Sakihama Y, et al. (2002) Nitric oxide production mediated by nitrate reductase in the green alga *Chlamydomonas reinhardtii*: an alternative NO production pathway in photosynthetic organisms. Plant Cell Physiol 43:290-7.

Saitou N and Nei M (1987) The neighbor-joining method: a new method for reconstructing phylogenetic trees. Mol Biol Evol 4:406-25.

Nei M and Gojobori T (1986) Simple methods for estimating the numbers of synonymous and 486 nonsynonymous nucleotide substitutions. Mol Biol Evol 3:418-26.

Hacker J and Kaper JB (2000) Pathogenicity islands and the evolution of microbes. Annu Rev 458 Microbiol 54:641-79.

Farlow A, et al. (2010) DNA double-strand break repair and the evolution 447 of intron density. Trends Genet 27:1-6.

Coyne K, et al. (2001) Assessing temporal and spatial variability in *Pfiesteria piscicida* distributions using molecular probing techniques. Aquat Microb Ecol 24: 275-285.

Ohwaki Y and Kaiser WM (2007) ., Plant Haemoglobins, Nitrate and Nitric Oxide: Old Players, New Games, *Progress in Botany* 68:261-87.

Zhang Z, et al. (2006) Detection of nitric oxide in culture media and studies of nitric oxide formation by marine microalgae, *Med Sci Monitor* 12:75-86.

International Search Report and Written Opinion dated Jun. 19, 2012, application No. PCT/US2011/044207.

Mukai M, et al. (2001) Flavohemoglobin, a globin with a peroxidase-like catalytic site. J Biol Chem 276:7272-7.

Nagase et al. (1997) Characteristics of biological NOx removal from flue gas in a Dunaliella tertiolecta culture system. Journal of Fermentation and Bioengineering. 83(5) 461-465.

Nagase et al. (1998) Improvement of microalgal NOx removal in bubble column and airlift reactors. Journal of Fermentation and Bioengineering. 86(4) 421-423.

Nagase et al. (2001). Uptake pathway and continuous removal of nitric oxide from flue gas using microalgae. Biochemical Engineering Journal. 7:241-246.

Nardini M, et al. (2007) Protein fold and structure in the truncated (2/2) globin family. Gene 398:2-11.

Oda T, et al. (1998) Lectin-induced 488 enhancement of superoxide anion production by red tide phytoplankton. Marine 489 Biology 131:383-390.

Olaizola (2003) Microalgal removal of CO2 from flue gases: Changes in medium pH and flue gas composition do not appear to affect the photochemical yield of microalgal cultures. Biotechnology and Bioprocess Engineering. 8:360-367.

Ouellet H et al. (2002) Truncated hemoglobin HbN protects *Mycobacterium bovis* from nitric oxide. Proc Natl Acad Sci USA 99:5902-5907.

Oullet, Y. et al. (2006). "Ligand interactions in the distal heme pocket of Mycobacterium tuberculosis truncated hemoglobin N: Roles of TyrB10 and GlnE11 residues." *Biochemistry*. 45: 8770-8781.

Pesce A et al. (2000) A novel two-over-two alpha-helical sandwich fold is characteristic of the truncated hemoglobin family. EMBO J 19:2424-34.

Poole RK and Hughes MN (2000) New functions for the ancient globin family: bacterial responses to nitric oxide and nitrosative stress. Mol Microbiol 36:775-83.

Rzhetsky A and Nei M (1992) Statistical properties of the ordinary least-squares, generalized least-squares, and minimum-evolution methods of phylogenetic inference. J Mol Evol 35:367-375.

Salvitti, et al. Evidence for the use of the nitrate reductase pathway as a source for the dissipation of excess excitation energy in Heterosigma akashiwo. ASLO 2009 Aquatic Sciences Meeting, Nice, France, Feb. 2009.

\* cited by examiner

Figure 2A

Full Length Genomic DNA Sequence for HaNR2-trHbN (SEQ ID NO: 1)

AAGCTTAGAAGGAGATATACATATGGCCCCTCCTTCTACGATCAAGATTGGCGGGTACACTTGCCCT
AAGGTTGACATCAGAGAGGTTGATCCTCGGGACGAAAAGACCCCCGATGACTGGATCCCTCGCCAC
CCTGACTTGGTCAGACTGACAGGTCGCCACCCCTTCAACTGCGAGCCTCCGGTCATGGACCTGATGA
GCCATGGCTTCATCACCCCCACGTCCTTGCACTACGTACGCAACCACGGTGCGGCTCCAAATCTCGA
TTGGGACTCCCATCGTGTCAgAATCTCAGGCCTGGTAGACAAACCCATGGAACTATCGATGGCTGAC
TTCACCGACCCCACCAAGTTCGAGCAGGTATCTATTCCTGTGACCCTCGTGTGTGCTGGAAACCGGC
GCAAGGAGCAGAACTCGGTAAAGCAGGGcATTGGCTTcAACTGGGGgCNAGCGGCCGTGTCTACTA
GCGTATGGACTgGGGGTGAGGGTGAGGGATGTACTTGAATACTGNGGATtgAAATCACAGGATGAG
GGTGCCAATCATGTGTGCTTTGTTGGTGCAGACCCTCTTCCTGGTGGGTACTACGGGACCAGCATCA
TACGCCATGTGAGTACCTTACCAGGTTTACTTGAGTATGAGTGTACCAGTGCACCTCTCTACACAAAT
GAACTTCCATGCATAGTTAACCTCCTCTTAACACTACAGCATGGTGAACTGCTTCTAACATATGTAGC
TTTTCAACAACTTGATTTGTGGCCTAAATGTCTTGCCTTGCACTGTTTTCTCAGGCTGCCATGGACCC
CGCCTCTGACGTCATGCTGTGCTGGGAGCAGAACGGCGAGCGCCTGACCCCTGACCACGGCTATCC
CATCCGGCTGATCATCCCAGGCTACATTGGTGGTCGCATGGTCAAGTGGCTGACAGACATCTCTGTC
ACTGAAGTTGAGTCTGACAATCACTACCACTATCATGACAATAGAGTCCTGCCCCCTCAGATTGATGC
TGACACCGCCAAGGCAGATGGCTGGTGGTACAAGCCAGAATACATCATCAATGACCTGAACATCAAT
TCTGCTATCACCTCACCAGCTCATGACGAGGTCGTGACCATCATCCCTGGGCAGAAAGCAACTTACG
CCTGCAAGGGGTACGCCTACTCAGGTGGTGGGCGCAAGGTGACTCGTGTGGAGCTGAGCTTCGATG
AGGGTGAGACTTGGGAGCTGACCACACTGACGCACCCGGAGCGGCCAACACGGGCGGGCAAGCAC
TGGTGCTGGTGCTTCTGGGAGTATGAGGTGCCCATCATGCGCATGCTGCGGGCCAAGCAGATGATG
GTGCGTGCCTGGGACACTGGCCTCAACACGCAGCCCATGAACTTCACCTGGAATGTGATGGGCATG
ATGAACAACTGCACATTCAAGGTGCGCATCCACGACGCCAGCGAGGGCAATGGTCTTTCCCTGAAGT
TTGAGCACCCCACCCAGCCTGGTGTGCTGCCAGGAGGCTGGATGGTGCCCAAGGTGGAGGTGCAG
GCGGCGGTGCAGGTGGAGAAGAAAGTGGAGGCTAAGGCTGGTGTGAAGTACTTCACAGAGGAGGA
GGTGGCCAAGCACACTGAGCGGGACGATGCGTGGTTTATCTACGATGGCAAGGTGTATGATGCAAC
TCCGTTCATGGACGATCACCCCGGCGGCGCAGACTCCATTCTTCTGACAGCAGGCGAGGACGCCAC
TGAGGAGTTTGACTCCCTGCATTCCGAGAAggCGAAGAAGATGCTGGATGACTACTACATTGGTGAG
CTGGGTACAGCACCTGCAGCGAGTGCCCCCCCCCCCTCCTGCTGTGAGCCTGTTTGAGAAGCTGGGT
GGGGGTGAAGCAGTCAATGCTGTGGTGAATAAGTTCTACGATGAAAAGGTGCTGAAGGATACCAGC
CTATCCCCAATCTTCGATGGCAAAGATGTTGAGTCCTTGAAAATGCATCAGGGTATGTTCCTTCAGTG
GGCACTTGGGGGGAGAACGGCTACACCGGGCGGTCCATGAAGGAGGCCCACGCTGGTTTGGGCA
TCACTGAGGCCCACTGGAACACGGTGTGTGGGCACCTGGTGGGCACACTGCAGGAGCTGGGTGTG
TCGGCGGCAGACATCGACACAGTGGTGTCCAAGGTGGCGCCCCTGAAGGACGACATTGTGGGGAC
TTCGGCGCTGAACCGACCCAAGGCGCTGAACAAGAAGAAGAAGATGGCGTTTGCGCTGGTGGAGC
GGGAGGAGATCACACACAATGTGCGGCGGCTACGGTTTGCGCTGCAGTCCCCGGAGCATGTTCTGG
GCTTGCCAGTGGGCCAGCACATGTTTGTCTCGGCCAAGATCGATGGTGCTCTTTGCATGCGCGCCTA
CACACCACTCACAGGTGACGAGGTCCAGGGGTACTTTGATCTGCTGATCAAGGTGTACTATGCAAAT
GAGCACCCCAAGTTCCCGGAGGGTGGCAAGATGAGCCAGCACCTGAACAGCTTGACCATTGGTCAG
ACCATTGACGTGCGCGGCCCTCTCGGCCACATTGACTACAAGGGCAAGGGTTTGTTTGATATTGACG
GCAAGGAGATCCAGTGTCGGGACATCCTGATGAtGGCAGGGGGCACAGGCATCACCCCCATGtGGC
AAGTAATGTCTGCTGTTCTTCGGGATGAGGCAGATTCCACCAAGCTGAACCTGATCTTTGCCAACAA
CACAGAGGATGACATCCTCCTGCAGGAAGAGCTGAATGATATGGACTCAGAGAACGAGCAATGCCA
GGTATACCACACAATAGCCACCCCAAAGAACCCTGAGACATGGTCTCAAGGAGTGGGCTTCATCACA
CAGGAGATGGTGGAGCAGCAGTTTGGTCCGGCTCGCGACGATGCGATTGTGTTCCTGTGCGGGCCT
CCCCCTATGATTAACTTTGCTTGTTTACCAGCCCTGGAGGCTCTGGGTTACAAGAAGGAGCAGATTTT
TCAGTTTTAGTGAATTCGAGCAAGCTTA

Figure 2B

Full Length cDNA Sequence for HaNR2-trHbN (SEQ ID NO: 2)

```
ATTCCCTTTCTTTTAGTCTGACCAATTGAGACAAAGATGGCCCCTCCTTCTACGATCAAGATTGGCGG
GTACACTTGCCCTAGGGTTGACATCAGAGAGGTTGATCCTCGGGACGAAAAGACCCCCGATGACTG
GATCCCTCGCCACCCTGACTTGGTCAGACTGACAGGTCGCCACCCCTTCAACTGCGAGCCTCCGGTC
ATGGACCTGATGAGCCATGGCTTCATCACCCCCACGTCCTTGCACTACGTACGCAACCACGGTGCGG
CTCCAAATCTCGATTGGGACTCCCATCGTGTCAGAATCTCAGGCCTGGTAGACAAACCCATGGAACT
ATCGATGGCTGACTTCACCGACCCCACCAAGTTCGAGCAGGTGTCTATTCCTGTGACCCTCGTGTGT
GCTGGAAACCGGCGCAAGGAGCAGAACTCGGTAAAGCAGGGCATTGGCTTCAACTGGGGCCAGC
GGCCGTGTCTACTAGCGTATGGACTGGGGTGAGGGTGAGGGATGTACTTGAATACTGTGGATTGAA
ATCACAGGATGAGGGTGCCAATCATGTGTGCTTTGTTGGTGCAGACCCTCTTCCTGGTGGGTACTAC
GGGACCAGCATCATACGCCATGCTGCCATGGACCCCGCCTCTGACGTCATGCTGTGCTGGGAGCAG
AACGGCGAGCGCCTGACCCCTGACCACGGCTATCCCATCCGGCTGATCATCCCAGGCTACATTGGT
GGTCGCATGATCAAGTGGCTGACAGACATCTCTGTCACTGAAGTTGAGTCTGACAATCACTACCACT
ATCATGACAACAGAGTCCTGCCCCCTCAGATTGATGCTGACACCGCCAAGGCAGATGGCTGGTGGT
ACAAGCCAGAATACATCATCAATGACCTGAACATCAACTCTGCCATCACCTCACCAGCTCATGACGA
GGTCGTGACCATCATCCCTGGGCAGAAAGCAACTTACGCCTGCAAGGGGTACGCCTACTCAGGTGG
TGGGCGCAAGGTGACTCGTGTGGAGCTGAGCTTCGATGAGGGTGAGACTTGGGAGCTGACCACACT
GACACACCCGGAGCGGCCTACACGGGCGGGCAAGCACTGGTGCTGGTGCTTCTGGGAGTATGAGG
TGCCCATCATGCGCATGCTGCGGGCCAAGCAGATGATGGTGCGTGCCTGGGACACTGGCCTCAACA
CGCAGCCCATGAACTTCACCTGGAATGTGATGGGTATGATGAACAACTGCACATTCAAGGTGCGCAT
CCACGACGCCAGCGAGGGCAATGGTCTTTCCCTGAAGTTTGAGCACCCCACCCAGCCTGGTGTGCT
CCCAGGAGGCTGGATGGTGCCCAAGGTGGAGGTGCAGGCGGCGGTGCAGGTGGAGAAGAAAGTG
GAGGCTAAGGCTGGTGTGAAGTACTTCACAGAGGAGGAGGTGGCCAAGCACACTGAGCGGGACGA
TGCGTGGTTTATCTACGATGGCAAGGTGTATGATGCAACGCCGTTCATGGACGATCACCCCAGCGG
CGCAGACTCCATTCTTCTGACAGCAGGCGAGGACGCCACTGAGGAGTTTGACTCCCTACATTCCGAG
AAGGCGAAGAAGATGCTGGATGACTACTACATTGGTGAGCTGGGTACAGCACCTGCAGCGAGTGCC
CCCCCCCTCCTGCTGTGAGCCTGTTTGAGAAGCTGGGTGGGGGTGAAGCAGTCAATGCTGTGGTG
AATAAGTTCTACGATGAAAAGGTGCTGAAGGATACCAGCCTATCCCCAATCTTCGATGGCAAAGATG
TTGAGTCCTTGAAAATGCATCAGCGTATGTTCCTTCAGTGGGTACTTGGGGGGGAAAACGGCTACAC
CGGGCGGTCCATGAAGGAGGCCCACGCTGGTTTGGGCATCACTGAGGCCCACTGGAACACGGTGT
GTGGGCACCTGGTGGGCACACTGCAGGAGCTGGGTGTGTCGGCGGCAGACATCGACACAGTGGTG
TCCAAGGTGGCGCCCCTGAAGGACGACGTTGTGGGGACTTCAGCGCTGAACCGACCCAAGGCGCT
GAACAAGAAGAAGAAGATGGCGTTTGCGCTGGTGGAGCGGGAGGAGATCACACACAATGTGCGGC
GGCTACGGTTTGCGCTGCAGTCCCCGGAGCATGTTCTGGGCTTGCCAGTGGGCCAGCACATGTTTG
TCTCGGCCAAGATCGATGGTGCTCTTTGCATGCGCGCCTACACACCACTCACAGGTGACGAGGTCCA
GGGGTACTTTGACCTGCTGATCAAGGTGTACTATGCAAATGAGCACCCCAAGTTCCCGGAGGGTGG
CAAGATGAGCCAGCACCTGAACAGCTTGACCATTGGTCAGACCATTGATGTGCGCGGCCCTCTCGG
CCACATTGACTACAAGGGCAAGGGTTTGTTTGATATTGACGGCAAGGAGATCCAGTGTCGGGACATC
CTGATGATGGCAGGGGGCACAGGCATCACCCCCATGTGGCAAGTAATGTCTGCTGTTCTTCGGGAT
GAGGCAGATTCCACCAAACTGAACCTGATCTTTGCCAACAACACAGAGGATGACATCCTCCTGCAGG
AAGAGCTGAATGATATGGACTCAGAGAACGAGCAATGCCAGGTATACCACACAATAGCCACCCCAAA
GAACCCTGAGACATGGTCTCAAGGAGTGGGCTTCATCACACAGGAGATGGTGGAGCAGCAGTTTGG
TCCGGCTCGCGACGATGCGATTGTGTTCCTGTGCGGGCCTCCCCCTATGATTAACTTTGCTTGTTTG
CCAGCCCTGGAGGCTCTGGGTTACAAGAAGGAGCAGATTTTTCAGTTTTAGTCAAGCCCTGATGTAT
TTAAAAATTATAATAATAATG
```

Figure 2C

Translated Protein Sequence for HaNR2-trHbN (SEQ ID NO: 3)

MAPPSTIKIGGYTCPRVDIREVDPRDEKTPDDWIPRHPDLVRLTGRHPFNCEPPVMDLMSHGFITPTSLH
YVRNHGAAPNLDWDSHRVRISGLVDKPMELSMADFTDPTKFEQVSIPVTLVCAGNRRKEQNSVKQGIG
FNWGPAAVSTSVWTGVRVRDVLEYCGLKSQDEGANHVCFVGADPLPGGYYGTSIIRHAAMDPASDVM
LCWEQNGERLTPDHGYPIRLIIPGYIGGRMIKWLTDISVTEVESDNHYHYHDNRVLPPQIDADTAKADG
WWYKPEYIINDLNINSAITSPAHDEVVTIIPGQKATYACKGYAYSGGGRKVTRVELSFDEGETWELTTLT
HPERPTRAGKHWCWCFWEYEVPIMRMLRAKQMMVRAWDTGLNTQPMNFTWNVMGMMNNCTFKVRI
HDASEGNGLSLKFEHPTQPGVLPGGWMVPKVEVQAAVQVEKKVEAKAGVKYFTEEEVAKHTERDDAW
FIYDGKVYDATPFMDDHPSGADSILLTAGEDATEEFDSLHSEKAKKMLDDYYIGELG<u>TAPAASAPPPPAV
SLFEKLGGGEAVNAVVNKFYDEKVLKDTSLSPIFDGKDVESLKMHQRMFLQWVLGGENGYTGRSMKEA
HAGLGITEAHWNTVCGHLVGTLQELG</u>VSAADIDTVVSKVAPLKDDVVGTSALNRPKALNKKKKMAFAL
VEREEITHNVRRLRFALQSPEHVLGLPVGQHMFVSAKIDGALCMRAYTPLTGDEVQGYFDLLIKVYYANE
HPKFPEGGKMSQHLNSLTIGQTIDVRGPLGHIDYKGKGLFDIDGKEIQCRDILMMAGGTGITPMWQVM
SAVLRDEADSTKLNLIFANNTEDDILLQEELNDMDSENEQCQVYHTIATPKNPETWSQGVGFITQEMVE
QQFGPARDDAIVFLCGPPPMINFACLPALEALGYKKEQIFQF

Figure 3A

Partial cDNA Sequence for CsNR2-trHbN (SEQ ID NO: 4)

GGATGATTAAATGGCTGACAGATATTGAAGTGACTTCCGAACAGTCCTCGAATCACTACCACTATCACG
ACAACCGAGTGCTTCCTCCACAAATTGATGCAGAAAGAGCATTAGCGGAGAAGTGGTGGTACAAGCCT
GAGTATATAATAAATGATTTGAACATTAATTCAGCCATTACTTCCCCAGCACACGGCGAAGAATTGGTA
CTATCATCATCGAACCAACAAASATACAAATGCAAAGGGTACGCATATTCTGGTGGAGGAAGGCAAGT
TACTCGAGTGGAGCTTTCTTTTGATGATGGGGAAACGTGGGATCTTTGCACATTGAACCACCCAGAAA
AGCCAACCAAAGCTGGTAAATATTGGTGTTGGTGCTTTTGGGAATATGATGTATCTATCCTGAAGCTAG
TTCGTAGCAAGCAAATGATGGTTCGGGCATGGGACACGGGTCTTAACACTCAACCAATGAATTTTACAT
GGAATGTCATGGGCATGATGAACAACAGCACTTTCAAGGTCAAAATTGATGCTCGTACAACCCAAACC
GCTGAGTCTTTAAAGTTTTCATTAGCTTTTGAACACCCAACACAACCAGGAGCWTTGCCAGGAGGTTG
GATGGTACCCAAAattGAGTCCCRACAAACAGAGCACAAGAAGGCTGAAACAAAAGATGTGGGCAAAG
GGAACAGGAAGCYGTATCCTTTGGAAGAAGTTGCAAAACACACTACAAAGGAAGACTGCTGGTTTGTA
TATGATGGCAAAGTTTTTGACAGTACAAGCTTCATGGATGATCATCCTGGTGGTGCTGATAGCATACTC
CTTACTGCCGGAGAAGATGCAACAGAAGARTTTGATTCTTTGCACTCAGAGAAAGCYCGCAAAATGCTT
GATAACTATTACATTGGAGATCTTGCCTCAGAAGATGCAGTAGAGGTGCAAAGGAATGCATTGCCTGG
AARAaaGAGTRGCCAAGTGAGCTTGTATGAGAAAGTTGGGGGTGAAGCTGCAATCCAAGCTGTAGTTG
AGAAATTTTACGAAGAAAAAGTTTTGAAAGACAACCTGCTGAGTCCAATCTTTGAGTCTCGTGACATTA
AGTCTTTGAAACTTCACCAGAAACTATTTCTCAAGTATGCTCTGGGTGGGACAAAAGCCTACGATGGAA
GGTCGATGTCAGATGCTCACCGTGGATTGGGAATCAAAGAACCTCATTGGAAAGCTGTGTGTGGACAC
TYGGTGAACACGTTGACTGAGTTGGGTGTTTCTCGTGAACATATAGATGAAGTAGTGCAGAGAGTCCT
CCCTCTCCATGATGATATTGTTGAARCACCCTCTTCTGAAKTAGTAGAATCCAACCCAATTGCATTGGAT
AGGAAAAAGAAGAATGCTTTTGCCTTGTTAGAAAAAGTTCAAGTAAGCCACAACACCATCAAGCTTAGA
TTTGCTCTTCCAACTGATGATCACATCCTAGGTCTGCCCGTTGGRAAACACATGTTCATCAGTGCAAAG
ATCAATGGATCTATGTGCATGCGAGCATACACTCCAATCACAGGRGATGAAGTCAAGGGTCACTTTGA
TCTTGTCATCAAAGTTTACTTCAAAAATGAGCACCCCAAATTCCCTGAGGGTGGGAAGATGTCGCAATA
CCTTAATGAGTTACAACTTGGACAAACAATTGACGTCAGAGGCCCACTGGGACATATCAACTACCTTGG
GAAAGGAGAATTYAACATCGATGGTACCTCAATTTRTGYTTCTAACATTTGCATGATGGCAGGTGGAAC
AGGRATTACTCCAATGTTTCAAGTTATTTCTGCAATCTTACGGGATGCTGAAGATTTCACAAATGTTTTC
TTGATATATGCAAACAATACTGAAGATGATATCCTYTTGCTGGAGGAGTTAGATCAAATGTCCAAAAGT
CAAAACTGCTCGATATTCCATACCTTAGCAACACCCMAAAATTCAGAGGTTTGGAAAGGAGGGGTGGG
ATTTATTACAGAAGACATGGTCAAACAGAATTTCC

Figure 3B

Translated Protein Sequence for CsNR2-trHbN (SEQ ID NO: 5)

MIKWLTDIEVTSEQSSNHYHYHDNRVLPPQIDAERALAEKWWYKPEYIINDLNINSAITSPAHGEELVLS
SSNQQXYKCKGYAYSGGGRQVTRVELSFDDGETWDLCTLNHPEKPTKAGKYWCWCFWEYDVSILKLV
RSKQMMVRAWDTGLNTQPMNFTWNVMGMMNNSTFKVKIDARTTQTAESLKFSLAFEHPTQPGALPGG
WMVPKIESXQTEHKKAETKDVGKGNRKXYPLEEVAKHTTKEDCWFVYDGKVFDSTSFMDDHPGGADS
ILLTAGEDATEEFDSLHSEKARKMLDNYYIGDLASEDAVEVQRNALPGXKSXQVSLYEKVGGEAAIQAV
VEKFYEEKVLKDNLLSPIFESRDIKSLKLHQKLFLKYALGGTKAYDGRSMSDAHRGLGIKEPHWKAVCG
HXVNTLTELGVSREHIDEVVQRVLPLHDDIVEXPSSEXVESNPIALDRKKKNAFALLEKVQVSHNTIKLRF
ALPTDDHILGLPVGKHMFISAKINGSMCMRAYTPITGDEVKGHFDLVIKVYFKNEHPKFPEGGKMSQYLN
ELQLGQTIDVRGPLGHINYLGKGEFNIDGTSIXXSNICMMAGGTGITPMFQVISAILRDAEDFTNVFLIYA
NNTEDDILLLEELDQMSKSQNCSIFHTLATPXNSEVWKGGVGFITEDMVKQNF

Prior Art

Figure 5

Figure 7
A.
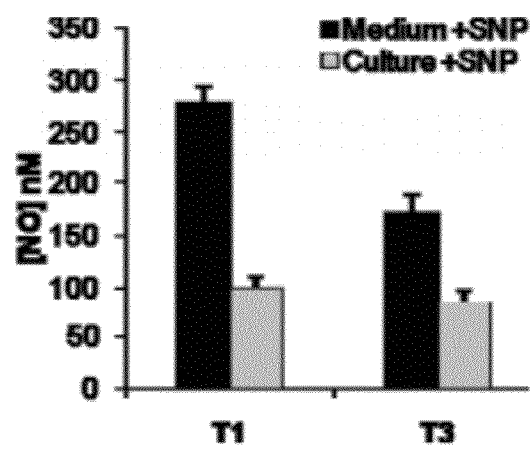
B.
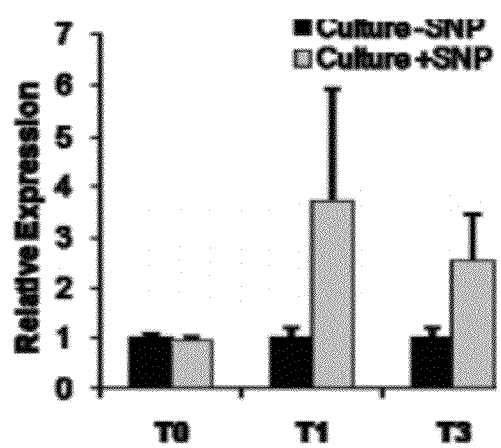
C.
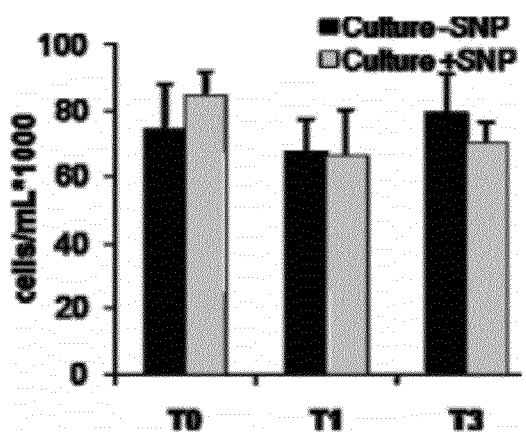

Figure 8
A.
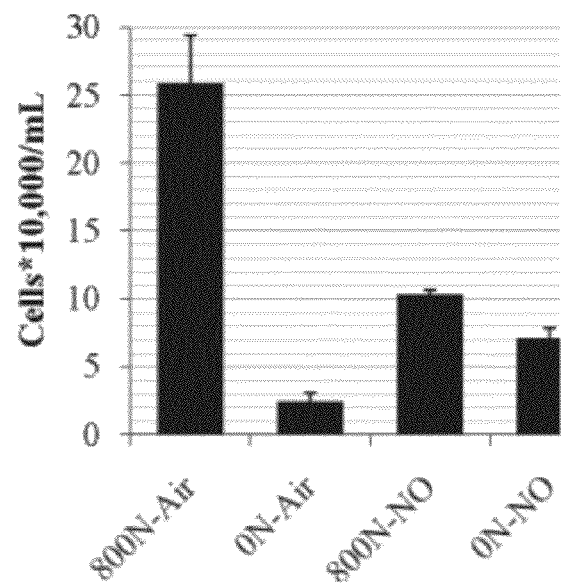
B.
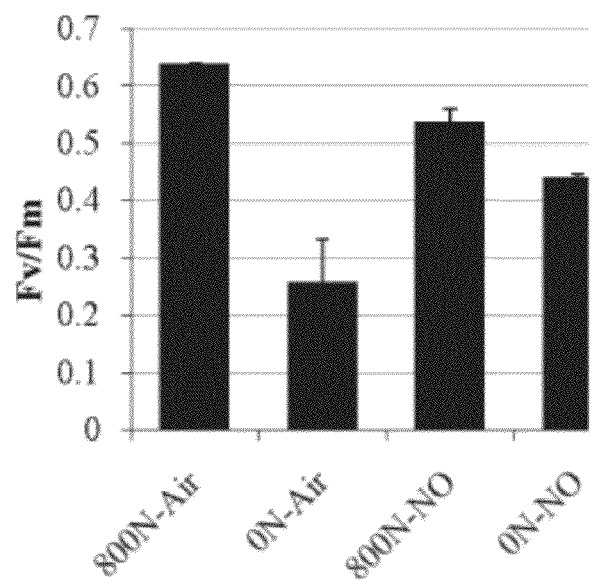

Figure 9
A.
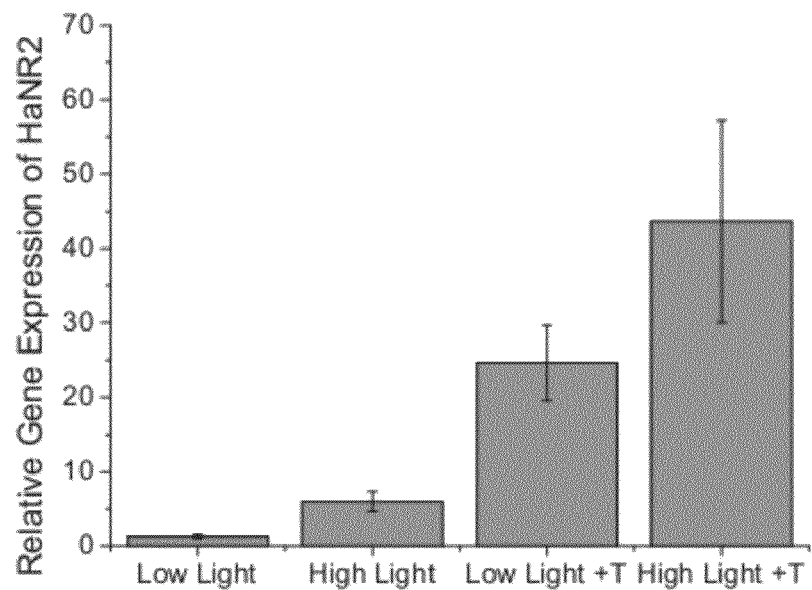
B.
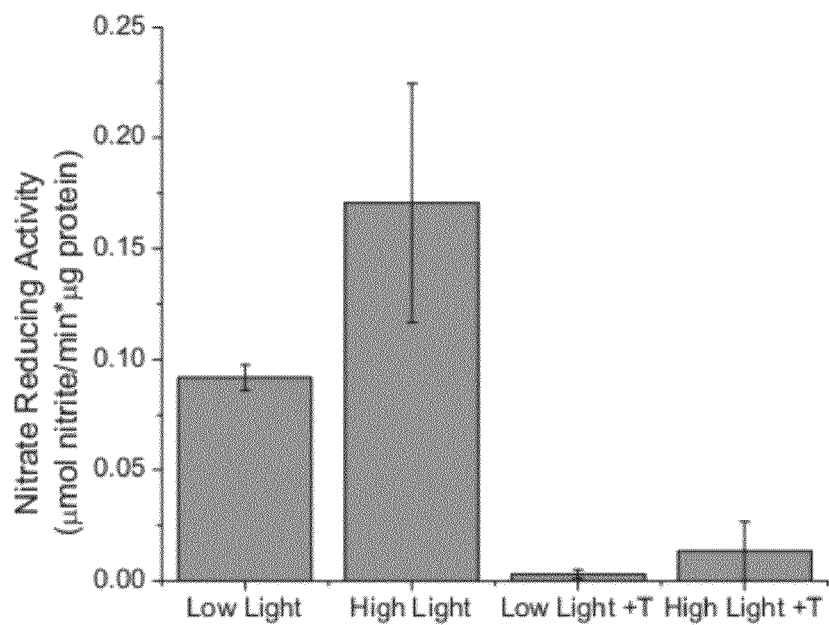

Figure 10
A.
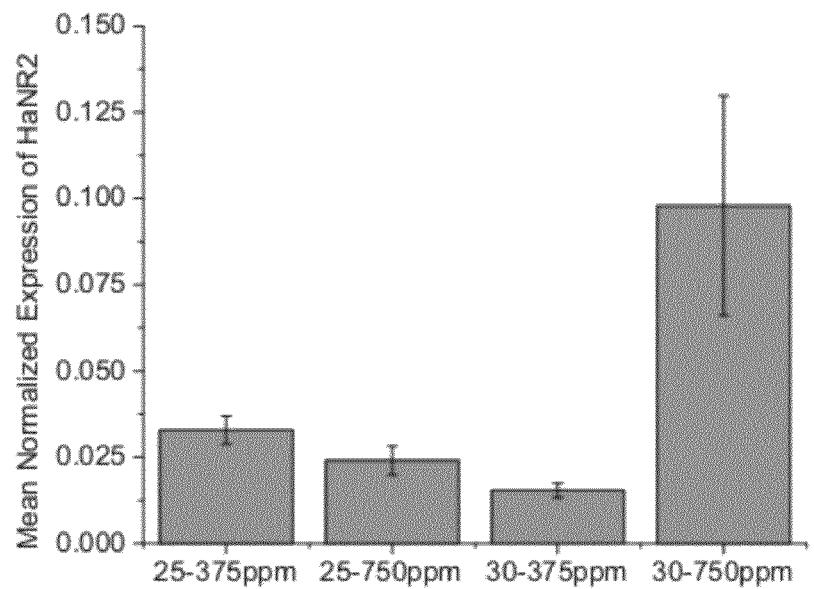
B.
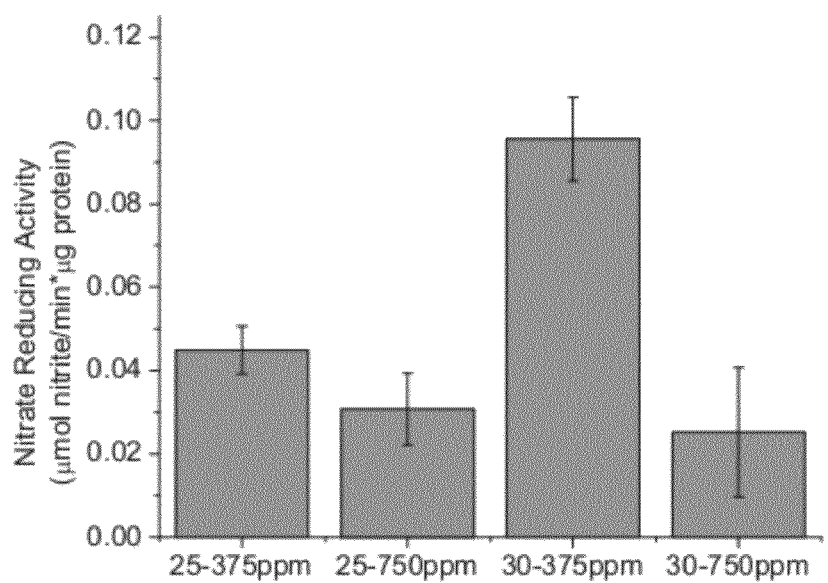

US 8,409,827 B2

NITRATE REDUCTASE FUSION PROTEINS AND USES THEREOF

CROSS-REFERENCE TO RELATED APPLICATION

This application claims the benefit of U.S. Provisional Application No. 61/364,583, filed Jul. 15, 2010, the content of which is incorporated herein by reference in its entirety for all purposes.

REFERENCE TO U.S. GOVERNMENT SUPPORT

This work is supported by a grant from the U.S. Environmental Protection Agency (Grant Nos. EPA STAR ECOHAB R83-3221 AND R83-1041) and a grant from the National Science Foundation (NSF) (Grant No. NA10NOS4780136). The United States has certain rights in the invention.

FIELD OF THE INVENTION

The invention relates generally to a novel fusion protein comprising a nitrate reductase (NR) and a truncated hemoglobin N (trHbN) domain, and the uses thereof for bioremediation of nitric oxide.

BACKGROUND OF THE INVENTION

Nitric oxide (NO) is a colorless and odorless gas. It is an important cell signaling molecule in mammals, including humans. It is also toxic as an air pollutant emitted mainly from combustion processes in, for example, fossil fuel power stations and automobile engines. Current methods for removing nitric oxide (NO) from flue gases rely on chemical processes with the disadvantages of expensive costs due to catalysts and chemicals, high energy requirements to sustain reaction temperatures, and negative environmental impacts from waste products such as urea and ammonia.

Alternative methods have been proposed to include complicated microbial bioreactors such as the BioDeNox process, which is a multiple step process that consumes ethanol, acetate, and/or Fe(II)EDTA$^{2-}$ as electron donors. This process is limited by the oxidation of Fe(II) to Fe(III) by oxygen, requires energy to sustain reaction temperatures of 140° F., and has a low NO removal efficiency of 40-70%.

Previous studies on the suitability of algal species for bioremediation of nitric oxide in flue gas are limited. The results of these studies have concluded that the species tested can only sustain removal of 40-65% nitric oxide for very short periods (10-15 days). The reported mechanism for nitric oxide removal in these studies relied on the pre-autooxidation of nitric oxide to nitrate and nitrite in the media in the presence of oxygen. The algal species tested then assimilated the nitrate/nitrite as nitrogen sources. Nitric oxide itself is highly toxic to cells, and the short durations of these previous experiments (10-15 days) suggest that those algal species did not have a method to metabolize nitric oxide directly.

There remains a need for an environmentally friendly and sustainable bioremediation of nitric oxide with great NO removal efficiencies.

SUMMARY OF THE INVENTION

The present invention relates to a novel fusion protein comprising a nitrate reductase (NR) and a truncated hemoglobin N (trHbN) domain, and uses thereof for bioremediation of nitric oxide.

An isolated fusion protein comprising a nitrate reductase (NR) and a truncated hemoglobin N (trHbN) domain is provided. The fusion protein may be capable of reducing nitric oxide. It may also be capable of converting nitric oxide to nitrate and nitrite.

The fusion protein may comprise a polypeptide having an amino acid sequence at least 90% identical to SEQ ID NO: 3 or 5, or a variant thereof. The fusion protein may be derived from a raphidophyte. The genus is selected from the group consisting of genus *Heterosigma*, *Chattonella*, *Fibrocapsa*, and *Viridilobus*. The raphidophyte may be *Heterosigma akashiwo*, *Chattonella subsalsa*, *C. marina*, *C. antigua*, *Fibrocapsa japonica*, or *Viridilobus marinus*.

A composition for reducing nitric oxide is also provided. The composition comprises an effective amount of a fusion protein, wherein the fusion protein comprises a nitrate reductase (NR) and a truncated hemoglobin N (trHbN) domain. The fusion protein may be capable of converting nitric oxide to nitrate and nitrite. The fusion protein may comprise a polypeptide having an amino acid sequence at least 90% identical to SEQ ID NO: 3 or 5, or a variant thereof. The fusion protein may be derived from a raphidophyte. The raphidophyte is selected from the group consisting of genus *Heterosigma*, *Chattonella*, *Fibrocapsa*, and *Viridilobus*. The raphidophyte may be *Heterosigma akashiwo*, *Chattonella subsalsa*, *C. marina*, *C. antigua*, *Fibrocapsa japonica*, or *Viridilobus marinus*.

A method for reducing nitric oxide is further provided. The method comprises applying an effective amount of a fusion protein, wherein the fusion protein comprises a nitrate reductase (NR) and a truncated hemoglobin N (trHbN) domain. The fusion protein may reduce nitric oxide by at least 50%. It may convert nitric oxide to nitrate and nitrite. The fusion protein may comprise a polypeptide having an amino acid sequence at least 90% identical to SEQ ID NO: 3 or 5, or a variant thereof. The fusion protein may be derived from a raphidophyte. The raphidophyte may be selected from the group consisting of genus *Heterosigma*, *Chattonella*, *Fibrocapsa*, and *Viridilobus*. The raphidophyte may be *Heterosigma akashiwo*, *Chattonella subsalsa*, *C. marina*, *C. antigua*, *Fibrocapsa japonica*, or *Viridilobus marinus*.

BRIEF DESCRIPTION OF THE DRAWINGS

FIG. 2 shows (A) the full length genomic DNA sequence (SEQ ID NO: 1), (B) the corresponding full length cDNA sequence (SEQ ID NO: 2), and (C) the corresponding translated amino acid sequence (SEQ ID NO: 3) for the NR2-trHbN fusion protein derived from *H. askashiwo* (HaNR2-trHbN). The underlined sequence reflects the trHbN domain.

FIG. 3 shows (A) a partial cDNA sequence (SEQ ID NO: 4) missing about 750-900 bases from the 5' end of the sequence, and (B) the corresponding translated protein sequence (SEQ ID NO: 5) for the NR2-trHbN fusion protein derived from *C. subsalsa* (CsNR2-trHbN). The underlined sequence reflects the trHbN domain.

FIG. 5 shows translated amino acid sequence alignment of the trHbN domain of NR2-trHbN with mycobacterial trHbN. Features characteristic of trHb structure are indicated: boxed residues are essential to the structure of the trHb fold, shaded residues are important to the formation of a hydrophobic ligand access tunnel, key active site residues are marked in black (Vuletich and Lecomte 2006). Symbols directly above the sequences indicate strictly conserved residues (*) and two levels of highly conserved substitutions (: and •) according to ClustalW2 annotation (Chema 2003; Larkin et al. 2007). Helix designations are denoted above the alignment following notations previously described in Lama et al. (2009). The sequence of the H-helix included in the HaNR1 hinge 2 region is indicated by a horizontal box for the *Heterosigma akashiwo* sequence only.

FIG. 7 shows the effect of nitric oxide on the expression of HaNR2-trHbN by adding a chemical nitric oxide (NO) donor, sodium pentacyanonitrosylferrate (II) (aka: sodium nitroprusside; SNP), to *Heterosigma akashiwo*. FIG. 7A shows the concentration of the dissolved NO in controls (cell free medium+SNP) and treatment cultures (*H. akashiwo* culture+SNP) at 1 hour (T1) and 3 hours (T3) after the addition of SNP. FIG. 7B shows the relative expression of NR2-trHbN in *H. akashiwo* control (−SNP) and treatment (+SNP) cultures before the addition of SNP (T0) and at 1 hour (T1) and 3 hours (T3) after the addition of SNP. Transcript abundance was calculated relative to the average abundance of controls at each time point. FIG. 7C shows the cell numbers at T0, T1, and T3 for *H. akashiwo* control (−SNP) and treatment (+SNP) cultures. Data plotted are mean values+SD (n=3).

FIG. 8 shows (A) biomass and (B) Fv/Fm on day 6 of batch growth after treatment with 800 μM $NaNO_3$/Ambient Air (800N-Air, control); 0 μM $NaNO_3$/Ambient Air (0N-Air); 800 μM $NaNO_3$/300 ppm NO (800N-NO); or 0 μM $NaNO_3$/300 ppm NO (0N-NO). Error bars represent standard deviation of replicates (n=3).

FIG. 9 shows (A) relative gene expression of HaNR2-trHbN and (B) nitrate reducing activity in *H. akashiwo* cultures subjected to low light (60 μmol quanta $m^{-2}s^{-1}$) and high light (785 μmol quanta $m^{-2}s^{-1}$) with and without the addition of sodium tungstate. T=Sodium tungstate.

FIG. 10 shows (A) relative gene expression HaNR2-trHbN and (B) nitrate reducing activity in *H. akashiwo* cultures grown at each of the following four conditions: 25° C. and 375 ppm $CO_2$, 25° C. and 750 ppm $CO_2$, 30° C. and 375 ppm $CO_2$, 30° C. and 750 ppm $CO_2$.

DETAILED DESCRIPTION OF THE INVENTION

Figure 1:
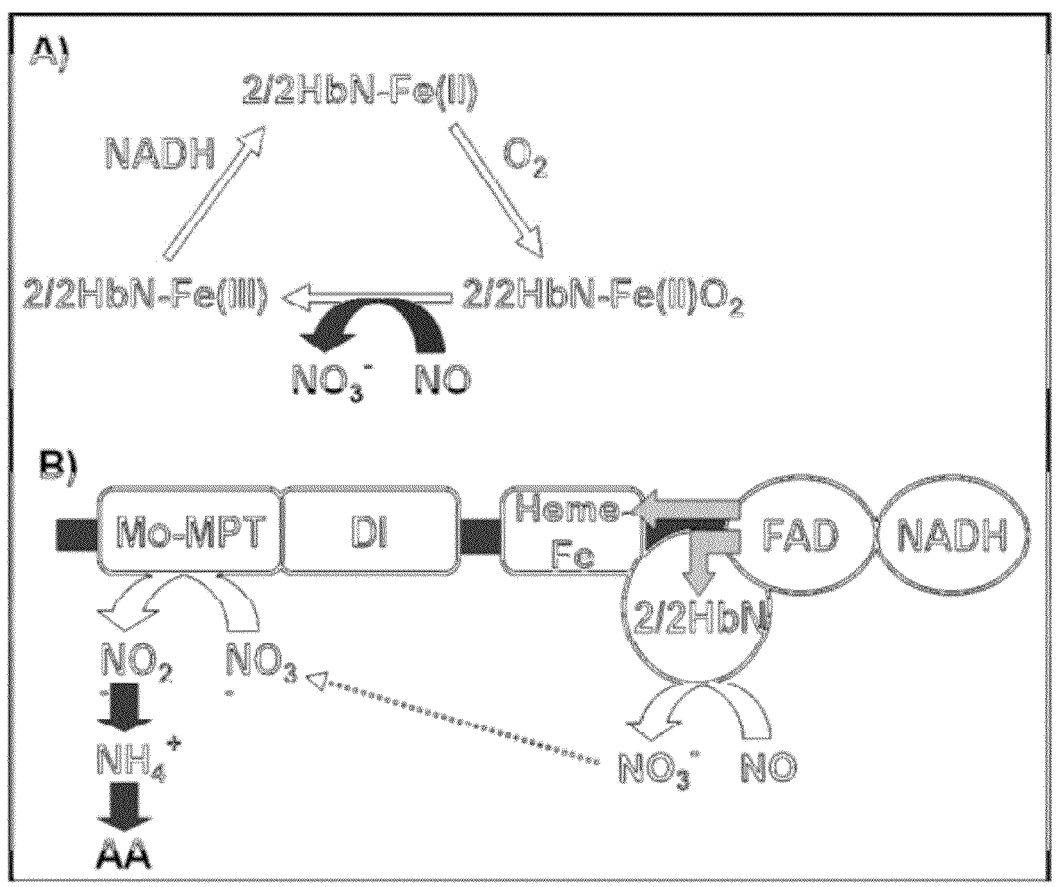
FIG. 1 illustrates a proposed mechanism for dual nitric oxide dioxygenase (NOD) and nitrate reductase activities by NR2-trHbN. (A) Mechanism of the NOD reaction known for mycobacterial group I truncated hemoglobins (trHbNs). Reductant is essential for the regeneration of active trHbN-Fe(II). (B) Proposed mechanism of NR2-trHbN coupling NOD and nitrate reductase activities. Electrons supplied by the FAD/NADH reductase domain (shaded arrows) may be used for nitrate reduction at the molybdenum-molybdopterin (MO-MPT) site and used for rapid regeneration of the active form of trHbN necessary for NO reactivity. Nitrate supplied by the detoxification of NO may be captured for reduction at the Mo-MPT site for incorporation as cellular nitrogen

The present invention is based on the discovery that a novel fusion protein, comprising a nitrate reductase (NR) and a truncated hemoglobin N (trHbN) domain, is capable of reducing nitric oxide to nitrate and nitrite.

The terms "protein" and "polypeptide" are used herein interchangeably, and refer to a polymer of amino acid residues with no limitation with respect to the minimum length of the polymer. The definition includes both full-length proteins and fragments thereof, as well as modifications thereof (e.g., glycosylation, phosphorylation, deletions, additions and substitutions).

The term "derived from" used herein refers to the origin or source, and may include naturally occurring, recombinant, unpurified or purified molecules.

The term "variant" of a protein as used herein refers to a polypeptide having an amino acid sequence that is the same as the amino acid sequence of the protein except having at least one amino acid modified, for example, deleted, inserted, or replaced. The variant may have an amino acid sequence at least about 80%, 90%, 95%, or 99%, preferably at least about 90%, more preferably at least about 95%, identical to the amino acid sequence of the protein.

The term "about" as used herein when referring to a measurable value such as an amount, a percentage, and the like, is meant to encompass variations of +20% or +10%, more preferably +5%, even more preferably +1%, and still more preferably +0.1% from the specified value, as such variations are appropriate.

According to one aspect of the present invention, an isolated fusion protein is provided. The fusion protein comprises a nitrate reductase (NR) and a truncated hemoglobin (trHb). The fusion protein may be able to reduce or remove nitric oxide. It may also be able to convert nitric oxide to nitrate and nitrite.

The nitrate reductase (NR) is a protein or polypeptide that can catalyze the reduction of nitrate to nitrite. It may be derived from any eukaryotic nitrate reductase. For example, it may comprise eight sequence regions or domains: (i) an N-terminal sequence, (ii) a catalytic active site for nitrate reduction incorporating a molybdenum-molybdopterin cofactor (Mo-MPT), (iii) a dimer interface (DI) region, (iv) a variable hinge 1 region, (v) a cyt b5-binding domain incorporating heme-Fe, (vi) a variable hinge 2 region, (vii) an FAD-binding domain, and (viii) an NADH-binding domain at the C-terminus. (Campbell 2001).

The truncated hemoglobin (trHb, also known as 2/2Hbs) is a small hemeprotein found in bacteria, ciliates, algae or plants. The trHb comprises a 2-on-2 α-helical fold, and may catalyze the reduction of nitric oxide to nitrate. It may be any member of the three paralogous groups, group I (trHbN), group II (trHbO), and group III (trHbP), preferably a trHbN domain.

The fusion protein of the present invention may be derived from a raphidophyte. The raphidophyte may be in genus *Heterosigma*, *Chattonella*, *Fibrocapsa*, and *Viridilobus*. Examples of raphidophytes include species *Heterosigma akashiwo*, *Chattonella subsalsa*, *C. marina*, *C. antigua*, *Fibrocapsa japonica*, and *Viridilobus marinus*.

Novel hybrid proteins (NR2-trHbN) in the raphidophytes, *Heterosigma akashiwo* and *Chattonella subsalsa*, have been discovered. In these hybrid proteins, a complete trHbN domain is inserted within the hinge 2 domain between the heme-Fe and FAD domains of a traditional NR sequence (FIGS. 2 and 3), resulting in a novel NR2-trHbN sequence. This novel NR2-trHbN sequence was found in multiple strains of *H. akashiwo*, including toxic and nontoxic strains isolated from the east and west coasts of the United States (e.g., CCMP2808, CCMP2393, CCMP1914 and C1 21 R2) and also in *C. subsalsa* (CCMP 2191) isolated from the Delaware Inland Bays. This NR2-trHbN sequence may also exist in other algal species within the raphidophyte group.

In one embodiment, the fusion protein of the present invention comprises 9 sequence regions or domains spanning over 900 amino acid residues, including a complete trHbN domain inserted within the hinge 2 domain of a traditional NR sequence. The trHbN domain within the trHbN-NR2 fusion protein may use the reductant supplied by the NR2 portion of the fusion protein such that the trHbN-NR2 fusion protein may exhibit coupled nitric oxide dioxygenase (NOD) and nitrate reductase activities (FIG. 1B), which is similar to the NOD reaction known for mycobacterial group I truncated hemoglobins (trHbNs) (FIG. 1A). For example, nitrate produced by trHbN NOD activity would then be captured for reduction at the Mo-MPT site of NR2-trHbN for incorporation into cellular nitrogen.

In another embodiment, a HaNR2-trHbN fusion protein derived from *Heterosigma akashiwo*, comprising a nitrate reductase NR2 and a trHbN domain, is provided. The HaNR2-trHbN fusion protein may comprise a polypeptide having an amino acid sequence of SEQ ID NO: 3, or a variant thereof. The variant may have an amino acid sequence at least about 80%, 85%, 90%, 95%, or 99%, preferably at least about 90%, identical to SEQ ID NO: 3.

In yet another embodiment, a CsNR2-trHbN protein derived from *Chattonella subsalsa*, comprising a nitrate reductase NR2 and a trHbN domain, is provided. The CsNR2-trHbN fusion protein may comprise a polypeptide having an amino acid sequence of SEQ ID NO: 5, or a variant thereof. The variant may have an amino acid sequence at least about 80%, 85%, 90%, 95%, or 99%, preferably at least about 90%, identical to SEQ ID NO: 5.

An isolated nucleic acid molecule encoding a fusion protein of the present invention is also provided. The fusion protein comprises a nitrate reductase (NR) and a truncated hemoglobin N (trHbN) domain. The fusion protein may be derived from a raphidophyte, preferably, the HaNR2-trHbN or CsNR2-trHbN fusion protein.

The nucleic acid molecule of the present invention may comprise a nucleotide sequence of SEQ ID NO: 2 or 4, or a variant thereof. The variant may have an amino acid sequence at least about 80%, 85%, 90%, 95%, or 99%, preferably at least about 90%, identical to SEQ ID NO: 2 or 4. The nucleic acid molecule may be operably linked to a promoter element suitable for expression of the gene in the nucleic acid molecule. It may also be in an expression vector.

For each fusion protein according to the present invention, a cell producing such a fusion protein is provided. Such a cell may be prepared using any conventional technique known in the art. A culture of cells producing a fusion protein of the present invention may also be prepared using standard methods known in the art. Such a cell culture may be used for purifying and isolating the fusion protein.

For each nucleic acid according to the present invention, a cell comprising such a nucleic acid molecule is provided. Such a cell may be prepared using any conventional technique known in the art. A culture of cells comprising a nucleic acid molecule of the present invention may also be prepared using standard methods known in the art. Such a cell culture may be used for producing the fusion protein.

Cells of the present invention may be grown under conditions suitable for the expression and/or production of a fusion protein according to the present invention. The cells are preferably grown under high light of at least about 50, 100, 200, 300, 400, 500, 600, 700, 800, 900 or 1000 mmol quanta $m^{-2}s^{-1}$, more preferably at least about 700 µmol quanta $m^{-2}s^{-1}$. The cells may be growth in the presence of an inhibitor (e.g., sodium tungstate ($Na_2WO_4$)) of the Mo-MPT nitrate reduction center of the nitrate reductase (NR) in the fusion protein. The cells may be grown at 25° C., 30° C., or 35° C., preferably at 25° C. The cells may be growth under 375 ppm, 750 ppm, or 15% $CO_2$, preferably at 750 ppm $CO_2$.

The present invention may be applied in several ways for the bioremediation of nitric oxide pollution. It is not limited to bioremediation of nitric oxide, but also allows for additional commercial applications (e.g., production of nitrate/nitrite as a nutrient source for biomass and/or directly reducing costs associated with algal biofuel production).

In one embodiment, whole cell algal suspensions of species expressing NR2 (such as *H. akashiwo* and *C. subsalsa*) may be grown on flue gas emissions for simultaneous removal of nitric oxide and carbon dioxide. *H. akashiwo* has been previously reported as an appropriate algal species for production of algal biofuels. Combining the bioremediation capabilities of *H. akashiwo* (and like species) with the production of algal biomass for biofuels will reduce the costs associated with algal biofuel production and provide a platform for sustainable and realistic commercialization of algae-derived biofuels. Further, the NR2 gene may be used to genetically modify existing algal species used in the biofuels industry, permitting them to survive in high nitric oxide conditions and allowing them to serve as bioremediators of nitric oxide.

In another embodiment, an engineered enzymatic reactor with a suspension of purified NR2 protein (supplied with NADH as a reductant) may be used to remove nitric oxide from flue gas. Nitric oxide-free flue gas still containing carbon dioxide can be used as a carbon source for nitric oxide-sensitive algal biomass growth. Additionally, the nitrate and nitrite produced by an enzymatic reaction can be sequestered, and supplied to the algal biomass as a free nitrogen source (fertilizer).

According to another aspect of the present invention, a composition for reducing nitric oxide is provided. The composition comprises an effective amount of a fusion protein of the present invention. The fusion protein comprises a nitrate reductase (NR) and a truncated hemoglobin N (trHbN) domain.

The term "reducing" used herein means "removing a portion of or all of"

In a composition of the present invention, the fusion protein is present in an amount effective, or sufficient, to reduce, or remove a portion or all of, nitric oxide such that the amount or concentration of the nitric oxide is lowered. The fusion protein may reduce nitric oxide by at least about 10%, 20%, 30%, 40%, 50%, 60%, 70%, 80%, 90%, 95%, 99%, or 100%, preferably, at least about 20%, more preferably, at least about 50%.

In a composition according to the present invention, the fusion protein is capable of converting nitric oxide to nitrate and nitrite. The fusion protein may be derived from a raphidophyte. The raphidophyte may be in genus *Heterosigma, Chattonella, Fibrocapsa*, and *Viridilobus*. Examples of raphidophytes include species *Heterosigma akashiwo, Chattonella subsalsa, C. marina, C. antigua, Fibrocapsa japonica*, and *Viridilobus marinus*. The fusion protein may comprise a polypeptide having an amino acid sequence of SEQ ID NO: 3 or 5, or at least about 80%, 85%, 90%, 95%, or 99%, preferably at least about 90%, identical to SEQ ID NO: 3 or 5.

The composition may further comprise a culture of cells that produces a fusion protein of the present invention. The cells may be producing the fusion protein, or capable of producing the fusion protein. The cells may comprise a nucleic acid molecule encoding the fusion protein.

According yet another aspect of the present invention, a method for reducing nitric oxide is provided. The method comprises applying an effective amount of a fusion protein of the present invention. The fusion protein comprises a nitrate reductase (NR) and a truncated hemoglobin N (trHbN) domain.

In a method of the present invention, the fusion protein is present in an amount effective to reduce, or remove a portion or all of, nitric oxide such that the amount or concentration of the nitric oxide is lowered. The fusion protein may reduce nitric oxide by at least about 10%, 20%, 30%, 40%, 50%, 60%, 70%, 80%, 90%, 95%, 99%, or 100%, preferably, at least about 20%, more preferably, at least about 50%. The reduction may be maintained for a period of at least about 1, 2, 3, 4, 5, 6, 7, 8, 9, 10, 15, 20, 25, or 30 days In a method according to the present invention, the fusion protein is capable of converting nitric oxide to nitrate and nitrite. The fusion protein may be derived from a raphidophyte. The raphidophyte may be in genus *Heterosigma*, *Chattonella*, *Fibrocapsa*, and *Viridilobus*. Examples of raphidophytes include species *Heterosigma akashiwo*, *Chattonella subsalsa*, *C. marina*, *C. antigua*, *Fibrocapsa japonica*, and *Viridilobus marinus*. The fusion protein may comprise a polypeptide having an amino acid sequence of SEQ ID NO: 3 or 5, or at least about 80%, 85%, 90%, 95%, or 99%, preferably at least about 90%, identical to SEQ ID NO: 3 or 5.

The method may further comprise applying a culture of cells that produces a fusion protein of the present invention in an effective amount to reduce nitric oxide. The cells may be producing the fusion protein, or capable of producing the fusion protein. The cells may comprise a nucleic acid molecule encoding the fusion protein.

EXAMPLE 1

HaNR2-trHbN Fusion Protein

A NR2-trHbN fusion protein was purified from *Heterosigma akashiwo*, and its sequence was determined.

*Heterosigma akashiwo* (CCMP 2393) was obtained from the Provasoli-Guillard Center for the Culture of Marine Phytoplankton (CCMP; Boothbay Harbor, Me.). A stock culture was maintained in seawater diluted to a salinity of 20 and amended with f/2 nutrients (—Si) (Guillard 1975), grown at 25° C. and an irradiance of ~185 μmol quanta $m^{-2}s^{-1}$, and set to a 12:12 h light:dark cycle.

RNA was extracted from *Heterosigma akashiwo* (CCMP 2393) and reverse transcribed using oligo-dT-Heel primer (Coyne et al. 2004) as previously described in Coyne (2010). To obtain the 3' end of the sequence, cDNA was then used as template in 20 μL PCR reactions containing 0.2 mM dNTPs, 0.25 μM Heel primer (Coyne et al. 2004), 0.25 μM HaNR—F primer (Coyne 2010), 2.5 mM $MgCl_2$, 1× Taq polymerase buffer (Sigma, St. Louis, Ill. USA) and 0.5 units Jump-Start Taq Polymerase (Sigma). The reaction consisted of 35 cycles of 30 s at 94° C., 30 s at 56° C. and 2.5 min at 72° C., followed by a 5 min extension at 72° C. PCR products were cloned into pCR4 TOPO plasmid vector (Invitrogen, Carlsbad, Calif. USA) and sequenced using Big Dye Terminator Cycle Sequencing Ready Reaction Kit (Applied Biosystems, Foster City, Calif. USA).

The 5' end of the HaNR2-trHbN cDNA sequence was obtained as described in Coyne (2010) using the GeneRacer RACE Ready cDNA Kit (Invitrogen) and primer HaNR-954R (AAGCCCAGAACATGCTCCG) (SEQ ID NO: 6) for the initial PCR reaction. The GeneRacer 5' Nested Primer included in the kit and HaNRGlob-312R primer (GCTGG-TATCCTTCAGCACCT) (SEQ ID NO: 7) were used in a nested PCR reaction as described in Coyne (2010) followed by cloning and sequencing as above.

To obtain the genomic DNA sequence, DNA was extracted from a stock culture of *H. akashiwo* as previously described in Coyne et al. (2001). The full length NR gene was amplified by PCR using the following primers:

```
HaNRFull-F (SEQ ID NO: 8):
AAGCTTAGAAGGAGATATACATATGGCCCCTCCTTCTACGATCAAGATTG HaNRFull-R (SEQ ID NO: 9):
AAGCTTGCTCGAATTCACTAAAACTGAAAAATCTGCTCCTTCTTG
```

These primers were designed for recombinant protein expression, so the specific sequence that targets HaNR2-trHbN is underlined for clarity. PCR reactions consisted of 20 μA reactions containing 0.2 mM dNTPs, 0.5 μM each primer, 2.5 mM $MgCl_2$, 1× Taq polymerase buffer (Sigma) and 0.5 units Jump-Start Taq Polymerase (Sigma). The PCR cycle consisted of 40 cycles of 30 s at 94° C., 30 s at 60° C. and 3 min at 72° C., followed by a 5 min extension at 72° C. PCR products were cloned and sequenced as described above.

Figure 4:
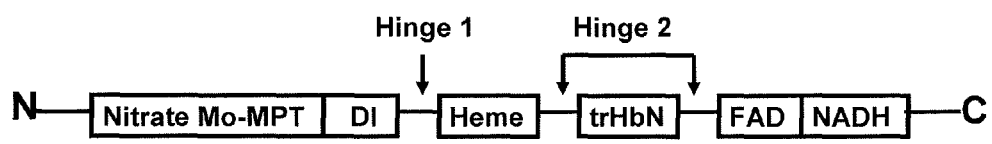
FIG. 4 illustrates a model of the domain architecture for the NR2-trHbN gene sequence. In NR2-trHbN, the truncated hemoglobin sequence (shown in grey) is inserted within the variable hinge 2 region of a traditional nitrate reductase (NR). NR is comprised of eight domains shown here, (i) an N-terminal domain, (ii) the molybdenum-molybdopterin cofactor (Mo-MPT) domain containing the catalytic active site for nitrate reduction, (iii) a dimer interface region (DI), (iv) a variable hinge 1 region, (v) a cyt b5-binding domain incorporating heme-Fe (Heme), (vi) a variable hinge 2 region, (vii) an FAD-binding domain, and (viii) an NADH-binding domain at the C-terminus (modified from Campbell 1999).

The full-length nucleotide sequence for HaNR1 (GenBank accession #GQ149451) was previously described as a traditional nitrate reductase (Coyne 2010). The full-length nucleotide sequence of HaNR2-trHbN (SEQ ID NO: 1) (FIG. 2A) derived from cDNA (SEQ ID NO: 2) (FIG. 2B) is 2,869 bases in length with a translated sequence of 936 amino acids (SEQ ID NO: 3) (FIG. 2C). The transcript included the domain regions as previously annotated in Coyne (2010) for HaNR1 with the addition of a 321-base nucleotide insertion (following nucleotide 1635 in HaNR1) in the hinge 2 region separating the cyt b5-binding domain from the FAD-binding domain (FIG. 4). The insertion in HaNR2-trHbN encodes a translated amino acid sequence of 107 amino acids. A direct repeat of 9 nucleotide bases (GAGCTGGGT) was found to flank the 321-base insertion in HaNR2-trHbN, whereas a single copy of this sequence was observed in HaNR1 at the insertion site (nucleotides 1627-1635 in HaNR1). Excluding the insert, the full-length cDNA sequence of HaNR2-trHbN is identical to HaNR1. The full-length gene sequence of HaNR2-trHbN was also obtained from genomic DNA. The gene sequence was found to contain the 321-base nucleotide insertion in the hinge 2 region and a single intron of 182 bases located within the Mo-MPT domain (following nucleotide 621 in HaNR1).

EXAMPLE 2

CsNR2-trHbN Fusion Protein

A CsNR2-trHbN fusion protein was purified from *Chattonella subsalsa*, and its sequence was determined.

*Chattonella subsalsa* (CCMP 2191) was obtained from the Provasoli-Guillard Center for the Culture of Marine Phytoplankton (CCMP; Boothbay Harbor, Me.). A stock culture was maintained in seawater diluted to a salinity of 20 and amended with f/2 nutrients (—Si) (Guillard 1975), grown at 25° C. and an irradiance of ~185 μmol quanta m$^{-2}$s$^{-1}$, and set to a 12:12 h light:dark cycle.

*Chattonella subsalsa* (CCMP2191) was cultured in f/2 medium and DNA was extracted as described in Coyne et al. (2001). A fragment of the NR gene was amplified by PCR using degenerate primers designed from conserved regions of NR. PCR reactions consisted of 20 μL reactions containing 0.2 mM dNTPs, 0.5 μM each primer NR231F (ATHGGNG-GNMGNATGATHAARTGG) (SEQ ID NO: 10) and NR394R (RTTRTTCATCATNCCCAT) (SEQ ID NO: 11), 2.5 mM MgCl$_2$, 1× Taq polymerase buffer (Sigma) and 0.5 units Jump-Start Taq Polymerase (Sigma). The PCR cycle consisted of 40 cycles of 30 s at 94° C., 30 s at 54° C. and 1 min at 72° C., followed by a 5 min extension at 72° C. PCR products were cloned and sequenced as described above.

To obtain the 3' end of the CsNR2-trHbN cDNA sequence, total RNA was reverse transcribed as described for *H. akashiwo* above. cDNA was then used as template in 20 μL PCR reactions containing 0.2 mM dNTPs, 0.25 μM Heel primer (Coyne et al. 2004), 0.25 μM CsNR-F2 primer (TTC-CGAACAGTCCTCGAATC) (SEQ ID NO: 12), 2.5 mM MgCl$_2$, 1× Taq polymerase buffer (Sigma) and 0.5 units Jump-Start Taq Polymerase (Sigma). The reaction consisted of 35 cycles of 30 s at 94° C., 30 s at 56° C. and 2 min at 72° C., followed by a 5 min extension at 72° C. PCR products were cloned and sequenced as described above.

A partial sequence of 2,248 bases was obtained for the CsNR2-trHbN cDNA sequence (SEQ ID NO: 4) (FIG. 3A) from *Chattonella subsalsa*. This sequence spans the DI domain through the C-terminus, and was also found to include a 342-base nucleotide sequence in the hinge 2 region with similarity to the insert described for HaNR2-trHbN. A partial sequence of 611 bases was also obtained from genomic DNA, which contains a single intron of 95 bases located within the DI domain following nucleotide 218.

EXAMPLE 3

Phylogenetic Analysis and Alignment of trHbN Region of HaNR2

Figure 5:
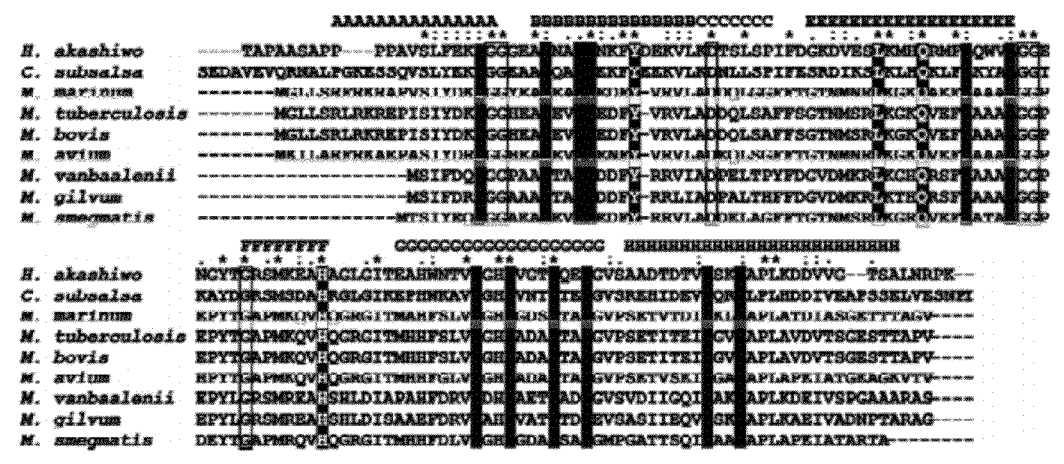

The boundaries for the amino acid sequence of the trHbN domain in HaNR2-trHbN were initially defined to include the 107 amino acids inserted in HaNR2-trHbN that were excluded from HaNR1. However, alignment with other trHb sequences (FIG. 5) revealed that the H-helix of the trHbN domain was also included in the HaNR1 sequence (Coyne 2010). Therefore, a total of 137 amino acids including the H-helix were used for phylogenetic and sequence analyses of the trHbN domain in HaNR2-trHbN. An NR1 gene was not found for *C. subsalsa*. Consequently, the boundary of the trHbN domain in CsNR2-trHbN was defined by alignment with HaNR2-trHbN and a total of 148 amino acids were included in the analysis.

The nucleotide sequences for trHbN domains in both NR2-trHbNs were compared to sequences in the NCBI protein database using the BLASTX algorithm (Altschul et al. 1997). Phylogenetic analyses were conducted in MEGA4 (Tamura et al. 2007). Database locations for sequences used in this analysis are listed in Online Resource 1 in Table Si. The evolutionary history for the translated amino acid sequences of the trHbN domains in HaNR2-trHbN and CsNR2-trHbN was inferred using the Minimum Evolution (ME) method (Rzhetsky and Nei 1992). The percentage of replicate trees in which the associated taxa clustered together in the bootstrap test (500 replicates) is shown next to each node (Felsenstein 1985). The tree is drawn to scale, with branch lengths in the same units as those of the evolutionary distances used to infer the phylogenetic tree. The ME tree was searched using the Close-Neighbor-Interchange (CNI) algorithm at a search level of 1. The Neighbor-joining algorithm (Saitou and Nei 1987) was used to generate the initial tree. All positions containing gaps and missing data were eliminated from the dataset. There were a total of 101 positions in the final dataset.

A subset of seven mycobacterial sequences identified in the phylogenetic analysis were aligned with the translated amino acid sequence of the trHbN domains in HaNR2-trHbN and CsNR2-trHbN by ClustalW2 (Chema 2003; Larkin et al. 2007) and annotated following helix designations previously given (Lama et al. 2009).

The similarity of FAD/NADH reductase domains of NR2-trHbN sequences to other enzymes was evaluated by comparison of the translated amino acid sequences to sequences in the NCBI protein database using the BLASTP algorithm (Altschul et al. 1997).

Figure 6:
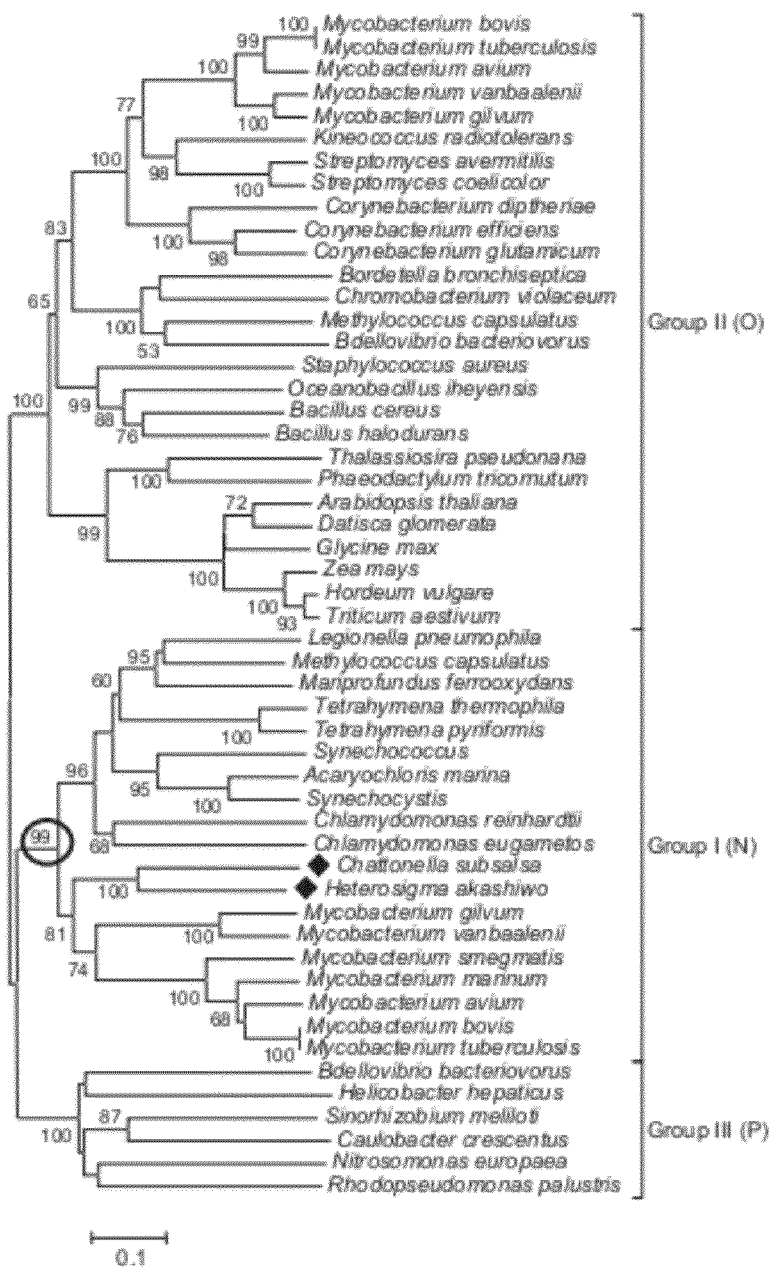
FIG. 6 shows a minimum evolution tree of representative sequences from trHb groups I (N), II (O) & III (P). Bootstrap values above 50% for 500 replications are noted at the nodes. Sequences for *Heterosigma akashiwo* and *Chattonella subsalsa* are indicated (♦), and the node that indicates the separation of trHbN sequences into two groups based on amino acid composition at the E7 position (leucine versus glutamine) is circled.

The translated amino acid sequence of the trHbN domains in HaNR2-trHbN and CsNR2-trHbN were shown to be homologous to trHbs by BLASTX (Altschul et al. 1997). Phylogenetic analysis of the amino acid sequences with 50 known trHb sequences representative of trHbN, trHbO and trHbP subtypes generated a robust tree with significant bootstrap values and placed the sequences within the group I (N-type) truncated hemoglobins (FIG. 6). The trHbN sequences in HaNR2-trHbN and CsNR2-trHbN were distinct from trHbN sequences of other algal and eukaryotic species and instead grouped strongly with trHbN sequences from the actinobacteria, *Mycobacterium* spp. Alignment of the trHbN domain from HaNR2-trHbN and CsNR2-trHbN with mycobacterial trHbN showed conserved residues that are involved in active site reactions as well as residues that are essential to the trHb 2-on-2 α-helical fold and residues that form a characteristic hydrophobic ligand access tunnel (FIG. 5; Vuletich and Lecomte 2006; Lama et al. 2009).

Notably, in NR2-trHbN and the actinobacteria sequences, leucine occupies the E7 residue in the active site, whereas glutamine is located at E7 in all other trHbN sequences analyzed. The node circled in FIG. 6 reflects this difference in active site composition between the two groups defined by the phylogenetic analysis. The alignment of HaNR2-trHbN with HaNR1 showed that the trHbN H-helix is part of the hinge 2 region of HaNR1 following the 9-nucleotide direct repeat (described above).

Amino acid sequences for the FAD/NADH reductase domains in HaNR2-trHbN and CsNR2-trHbN were also analyzed independently and found to be homologous to eukaryotic NR sequences.

EXAMPLE 4

Effect of Nitric Oxide on Expression of HaNR2-trHbN

*H. akashiwo* was grown semi-continuously in f/2 medium to maintain steady state growth for 8 days prior to the experiment. To examine the effect of NO on the expression of HaNR2-trHbN, triplicate cultures of *H. akashiwo* were treated with the chemical NO donor, sodium pentacyanonitrosylferrate (II) (SNP), at a final concentration of 0.4 mM SNP. Two sets of controls were included in this experiment: triplicate cultures not treated with SNP (for comparison of transcript abundance) and triplicate aliquots of cell-free f/2 medium treated with 0.4 mM SNP (for comparison of NO concentrations). Cell counts were determined by microscopy using a Neubauer Hemocytometer for control and SNP-treated cultures before the addition of SNP (T0), at 1 hour (T1) and 3 hours (T3) after the addition of SNP. NO generated by the chemical decomposition of SNP was measured electrochemically in treatment cultures and cell-free medium at T1 and T3 as previously described (Sakihama et al. 2002; Xing et al. 2005). Briefly, a NO-specific microsensor (ISO-NOP, World Precision Instruments, Sarasota, Fla.), capable of detecting NO in the range of 0.3 nM to 100 µM, was used to selectively measured NO in algal culture media. The method for sensor calibration according to the manufacturer's instructions for the chemical generation of NO was modified by diluting the calibration solution in 20 psu seawater. NO concentrations in treatment cultures (+SNP) and controls (cell-free medium+SNP) were then determined by linear regression analysis.

For transcript analysis, 50 mL of culture were collected from treatment (+SNP) and control (−SNP) cultures at T0, T1 and T3 and filtered onto 3.0 µm polycarbonate filters. The filters were submerged into buffer RLT (RNEasy Plant Mini Kit, Qiagen) and heated at 56° C. before freezing at −80° C. RNA was extracted using the RNEasy Plant Mini Kit (Qiagen) and resuspended in RNase-free water. The purity of total RNA was analyzed spectroscopically and RNA was treated with DNase I (Invitrogen) as previously described (Coyne and Cary 2005). Approximately 500 ng of DNase-treated total RNA was reverse transcribed with random hexamers using the Superscript III First Strand Synthesis System (Invitrogen). Duplicate reactions for each DNase-treated RNA sample without reverse transcriptase were also evaluated by PCR. Transcript abundances for HaNR2-trHbN and glyceraldehyde 3-phosphate dehydrogenase (HaGAP) as a reference gene were determined by quantitative real time-PCR using the Stratagene MX3005P Sequence Detection System (Agilent Technologies, Santa Clara, Calif.). cDNA was diluted 1:20 in LoTE [3 mM Tris-HCl (pH 7.5), 0.2 mM EDTA] and used as template in triplicate 10 µL reactions. Each reaction consisted of 14 diluted cDNA, 5 µL of SYBR Green Master Mix (Applied Biosystems), and either 0.9 µM HaNRGlob-239F primer (CTGTGAGCCT-GTTTGAGAAG) (SEQ ID NO: 13) and 0.3 µM HaNRGlob-312R primer (GCTGGTATCCTTCAGCACCT) (SEQ ID NO: 7) for HaNR2-trHbN analysis or 0.9 µM HaGAP-448F primer (Coyne 2010) and 0.3 µM HaGAP-638R primer (Coyne 2010) for HaGAP analysis. Cycling parameters were as follows: 10 min at 50° C., 2 min at 95° C., followed by 40 cycles of 15 s at 95° C., 30 s at 56° C., and 1 min at 60° C. The dissociation of duplex PCR products was monitored during a stepwise increase in temperature from 60° C. to 95° C. to evaluate reaction specificity. Average values of transcript abundance were determined by linear regression analysis of triplicate reactions. HaNR2-trHbN transcript abundances were calculated from a standard curve prepared from $1\times10^{-2}$ ng to $1\times10^{-6}$ ng of HaNR2-trHbN plasmid. NR transcript abundances were then normalized to HaGAP expression as described in Coyne (2010). Relative expression was then calculated as the ratio of the normalized transcript levels in each treatment to the average normalized transcript levels of controls.

For statistical analyses, standard deviations were calculated from the average of replicates (n=3), and means were compared using a one-way ANOVA followed by Tukey HSD post hoc testing using PAST v2.05 software (Hammer et al. 2001). Differences were determined to be statistically significant when p<0.05. Prior to analysis by ANOVA, data were assessed for normality and equality of variance. Raw data for relative gene expression did not meet assumptions of equal variance and were log transformed prior to statistical analysis.

Measurements of NO in cell-free medium (+SNP) showed that cells were exposed to nanomolar concentrations of NO in this experiment, with the highest NO concentration (277 nM) occurring at T1. NO concentrations were significantly lower in *H. akashiwo* cultures (+SNP) compared to cell-free medium (+SNP) (FIG. 7A), with a 64% reduction in NO at T1 (p<0.001) and a 51% reduction at T3 (p<0.007). HaNR2-trHbN transcript abundance in treatment cultures (+SNP) was significantly higher than control cultures (−SNP) at T1 and T3 (p<0.05; FIG. 7B). Additionally, cell numbers remained constant over the course of the experiment for cultures with and without SNP addition (FIG. 7C).

EXAMPLE 5

Biomass and Photosynthetic Efficiency after Treatment of *H. akashiwo* Cultures with NO Gas Goals of this experiment were to (i) show that *H. akashiwo* can initiate batch growth after exposure to 300 ppm NO and (ii) evaluate the potential of cells to utilize NO as a sole nitrogen source. Cultures were inoculated at 30,000 cells/mL in modified f/2 medium with or without nitrate supplied as a nitrogen source. After inoculation, cultures were treated with either ambient air (control) or 300 ppm NO gas balanced in $N_2$ for 16 hours at a flow rate of 100 mL/min. Growth was monitored over the following batch cycle for triplicate cultures in four treatments: 800 µM $NaNO_3$/Ambient Air (control); 0 µM $NaNO_3$/Ambient Air; 800 µM $NaNO_3$/300 ppm NO; or 0 µM $NaNO_3$/300 ppm NO.

On day 6 of batch growth, biomass and photosynthetic efficiency were compared (FIG. 8). Chlorophyll fluorescence of whole cells was read on a fluorescence induction and relaxation fluorometer (FIRe) to measure the ratio of variable fluorescence (Fv) to maximal fluorescence (Fm). Fv/Fm measurements quantify the efficiency of photosystem II and are used as an indicator of photosynthetic efficiency and general cell health. The interpretation of Fv/Fm values is species specific. As a general rule for *H. akashiwo*, an Fv/Fm of 0.6-0.7 indicates high efficiency, 0.5-0.6 is average and often observed in healthy laboratory cultures, 0.4-0.5 indicates a decline in photosystem II efficiency, and below 0.4 indicates severe stress.

800 µM $NaNO_3$/Ambient Air control cultures had the highest average biomass and Fv/Fm (0.64), while 0 µM $NaNO_3$/Ambient Air had the lowest average biomass and Fv/Fm (0.26), indicating that these cells were severely stressed under nitrogen starvation. 800 µM $NaNO_3$/300 ppm NO cultures maintained moderate Fv/Fm values (0.54) indicating that photosynthetic activity remained normal after exposure to NO gas. The average Fv/Fm for 0 µM $NaNO_3$/300 ppm NO (0.44) was above the 0.4 minimum cutoff and higher than air treated cells without nitrogen. It was also observed that 0 µM $NaNO_3$/Ambient Air cultures did not grow and instead formed non-motile spherical cysts, however, 0 µM $NaNO_3$/300 ppm NO did not encyst (data not shown). These results suggest that *H. akashiwo* is able to use NO as a nitrogen source for growth, but the mechanism of NO utilization was not determined. The observation that cells remained healthy throughout the growth cycle and can use NO gas as a source of nitrogen is promising, but data for long-term acclimation under constant NO supply is needed to truly assess the impact of NO on the growth and physiology of *H. akashiwo*.

EXAMPLE 6

Effect of Light on the Expression of HaNR2-trHbN

Cultures of *H. akashiwo* were subjected to shifts in irradiance from low light (60 μmol quanta $m^{-2}s^{-1}$) to high light (785 μmol quanta $m^{-2}s^{-1}$) with and without the addition of sodium tungstate ($Na_2WO_4$, an inhibitor of the Mo-MPT nitrate reduction center in NR). Samples were taken for gene expression analysis and nitrate reductase activity four hours after the shift to highlight. Data (FIG. 9) shows that expression of HaNR2 and nitrate reducing activity both increase in response to high light. In the presence of $Na_2WO_4$, nitrate reducing activity is abolished and the expression of HaNR2 increases greater than 60 times that of controls (FIG. 9). $Na_2WO_4$ blocks nitrate reduction at the Mo-MPT center but does not interfere with the flow of electrons to the trHbN domain in HaNR2 (FIG. 9).

EXAMPLE 7

Effect of Temperature and Carbon Dioxide on the Expression of HaNR2-trHbN

Cultures of *H. akashiwo* were grown at each of the following four conditions: 25° C. and 375 ppm $CO_2$, 25° C. and 750 ppm $CO_2$, 30° C. and 375 ppm $CO_2$, 30° C. and 750 ppm $CO_2$. Cultures were grown under these conditions for three 7-day batch cycles followed by 10 days of semi-continuous growth before sampling for gene expression analysis and nitrate reducing activity. The expression of HaNR2 was the lowest in 30° C. and 375 ppm $CO_2$, which was the condition that showed the highest nitrate reducing activity (FIG. 10). Furthermore, HaNR2 expression was the highest in the combined elevated temperature and $CO_2$ condition (30° C. and 750 ppm $CO_2$) (FIG. 10).

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

REFERENCES

Altschul S F et al. (1997) Gapped BLAST and PSI-BLAST: a new generation of protein database search programs. Nucleic Acids Res 25:3389-402.
Berges J (1997) Miniview: Algal nitrate reductases. Eur J Phycol 32:3-8.
Bonamore A et al. (2007) A novel chimera: the "truncated hemoglobin-antibiotic monooxygenase" from *Streptomyces avermitilis*. Gene 398:52-61.
Campbell W H (1999) Nitrate reductase structure, function and regulation: Bridging the gap between biochemistry and physiology. Annu Rev Plant Physiol Plant Mol Biol 50:277-303.
Campbell W H (2001) Structure and function of eukaryotic NAD(P)H:nitrate reductase. Cell Mol Life Sci 58:194-204.
Chema R (2003) Multiple sequence alignment with the Clustal series of programs. Nucleic Acids Res 31:3497-3500.
Coyne K, Hutchins D, Hare C, Cary S (2001) Assessing temporal and spatial variability in *Pfiesteria piscicida* distributions using molecular probing techniques. Aquat Microb Ecol 24:275-285.
Coyne K J, Burkholder J M, Feldman R A, Hutchins D A, Cary S C (2004) Modified serial analysis of gene expression method for construction of gene expression profiles of microbial eukaryotic species. Appl Environ Microbiol 70:5298-5304.
Coyne K J, Craig Cary S (2005) Molecular approaches to the investigation of viable dinoflagellate cysts in natural sediments from estuarine environments. J Eukaryot Microbiol 52:90-4.
Coyne K J (2010) Nitrate reductase (NR1) sequence and expression in the harmful alga *Heterosigma akashiwo* (Raphidophyceae). J Phycol 46:135-142.
Eckardt N A (2005) Moco Mojo: Crystal structure reveals essential features of eukaryotic assimilatory nitrate reduction. Plant Cell 17:1029-1031.
Felsenstein J (1985) Confidence limits on phylogenies: An approach using the bootstrap Evolution 39:783-791.
Gardner P R et al. (2000) Nitric-oxide dioxygenase activity and function of flavohemoglobins. Sensitivity to nitric oxide and carbon monoxide inhibition. J Biol Chem 275: 31581-7.
Gardner P R (2005) Nitric oxide dioxygenase function and mechanism of flavohemoglobin, hemoglobin, myoglobin and their associated reductases. J Inorg Biochem 99:247-66.
Guillard R R L (1975) In: Smith W L, Chanley M H (eds) Culture of Marine Invertebrate Animals. Plenum Press, New York, pp 26-60.
Kim D (2006) Nitric oxide synthase-like enzyme mediated nitric oxide generation by harmful red tide phytoplankton, *Chattonella marina*. J Plankton Res 28:613-620.
Kim D et al. (2008) Detection of nitric oxide (NO) in marine phytoplankters. J Biosci Bioeng 105:414-7.
Lama A, Pawaria S, Dikshit K L (2006) Oxygen binding and NO scavenging properties of truncated hemoglobin, HbN, of *Mycobacterium smegmatis*. FEBS Lett 580:4031-4041.
Lama A et al. (2009) Role of pre-A motif in nitric oxide scavenging by truncated hemoglobin, HbN, of *Mycobacterium tuberculosis*. J Biol Chem 284:14457-68.
Larkin M A et al. (2007) Clustal W and Clustal X version 2.0. Bioinformatics 23:2947-8.
Lecomte J T J, Vuletich D A, Lesk A M (2005) Structural divergence and distant relationships in proteins: evolution of the globins. Curr Opin Struct Biol 15:290-301.
Milani M, Pesce A, Ouellet H, Guertin M, Bolognesi M (2003) Truncated hemoglobins and nitric oxide action. IUBMB Life 55:623-7.
Mukai M, Mills C E, Poole R K, Yeh S R (2001) Flavohemoglobin, a globin with a peroxidase-like catalytic site. J Biol Chem 276:7272-7.
Nardini M, Pesce A, Milani M, Bolognesi M (2007) Protein fold and structure in the truncated (2/2) globin family. Gene 398:2-11.
Ouellet H et al. (2002) Truncated hemoglobin HbN protects *Mycobacterium bovis* from nitric oxide. Proc Natl Acad Sci USA 99:5902-7.
Pesce A et al. (2000) A novel two-over-two alpha-helical sandwich fold is characteristic of the truncated hemoglobin family. EMBO J. 19:2424-34.

Poole R K, Hughes M N (2000) New functions for the ancient globin family: bacterial responses to nitric oxide and nitrosative stress. Mol Microbiol 36:775-83.

Rzhetsky A, Nei M (1992) Statistical properties of the ordinary least-squares, generalized least-squares, and minimum-evolution methods of phylogenetic inference. J Mol Evol 35:367-375.

Saitou N, Nei M (1987) The neighbor-joining method: a new method for reconstructing phylogenetic trees. Mol Biol Evol 4:406-25.

Sakihama Y, Nakamura S, Yamasaki H (2002) Nitric oxide production mediated by nitrate reductase in the green alga *Chlamydomonas reinhardtii*: an alternative NO production pathway in photosynthetic organisms. Plant Cell Physiol 43:290-7.

Smagghe B J, Trent J T, Hargrove M S (2008) NO dioxygenase activity in hemoglobins is ubiquitous in vitro, but limited by reduction in vivo. PloS One 3:e2039.

Stolz J F, Basu P (2002) Evolution of nitrate reductase: Molecular and structural variations on a common function. Chembiochem 3:198-206.

Tamura K, Dudley J, Nei M, Kumar S (2007) MEGA4: Molecular Evolutionary Genetics Analysis (MEGA) software version 4.0. Mol Biol Evol 24:1596-9.

Vinogradov S N et al. (2005) Three globin lineages belonging to two structural classes in genomes from the three kingdoms of life. Proc Natl Acad Sci USA 102:11385-9.

Vinogradov S N, Moens L (2008) Diversity of globin function: enzymatic, transport, storage, and sensing. J Biol Chem 283:8773-7.

Vuletich D A, Lecomte J T J (2006) A phylogenetic and structural analysis of truncated hemoglobins. J Mol Evol 62:196-210.

Wittenberg J, Bolognesi M, Wittenberg B, Guertin M (2002) Truncated hemoglobins: A new family of hemoglobins widely distributed in bacteria, unicellular eukaryotes, and plants. J Biol Chem 277:871-4.

Xing L, Zhang Z-B, Liu C—Y, Wu Z-Z, Lin C (2005) Amperometric detection of nitric oxide with microsensor in the medium of seawater and its applications. Sensors 5:537-545.

Yeh S R, Couture M, Ouellet Y, Guertin M, Rousseau D L (2000) A cooperative oxygen binding hemoglobin from *Mycobacterium tuberculosis*. Stabilization of heme ligands by a distal tyrosine residue. J Biol Chem 275:1679-84.

Zhang Z, Liu C, Wu Z, Xing L, Li P (2006) Detection of nitric oxide in culture media and studies of nitric oxide formation by marine microalgae. Med Sci Monitor 12:75-86.

Zhou J, Kleinhofs A (1996) Molecular evolution of nitrate reductase genes. J Mol Evol 42:432-42.

---

What is claimed:

1. An isolated fusion protein comprising a nitrate reductase (NR) and a truncated hemoglobin N (trHbN) domain, wherein the fusion protein comprises a polypeptide having an amino acid sequence at least 90% identical to SEQ ID NO: 3 or 5.

2. The isolated fusion protein of claim 1, wherein the fusion protein is capable of reducing nitric oxide.

3. The isolated fusion protein of claim 1, wherein the fusion protein is capable of converting nitric oxide to nitrate and nitrite.

4. The isolated fusion protein of claim 1, wherein the fusion protein comprises a polypeptide having the amino acid sequence of SEQ ID NO: 3 or 5.

5. The isolated fusion protein of claim 1, wherein the fusion protein is derived from a raphidophyte.

6. The isolated fusion protein of claim 5, wherein the raphidophyte is selected from the group consisting of genus *Heterosigma*, and *Chattonella*.

7. The isolated fusion protein of claim 5, wherein the raphidophyte is selected from the group consisting of species *Heterosigma akashiwo*, and *Chattonella subsalsa*.

8. A composition for reducing nitric oxide, comprising an effective amount of an isolated fusion protein, wherein the fusion protein comprises a nitrate reductase (NR) and a truncated hemoglobin N (trHbN) domain, wherein the fusion protein comprises a polypeptide having an amino acid sequence at least 90% identical to SEQ ID NO: 3 or 5.

9. The composition of claim 8, wherein the fusion protein is capable of converting nitric oxide to nitrate and nitrite.

10. The composition of claim 8, wherein the fusion protein comprises a polypeptide having the amino acid sequence of SEQ ID NO: 3 or 5.

11. The composition of claim 8, wherein the fusion protein is derived from a raphidophyte.

12. The composition of claim 11, wherein the raphidophyte is selected from the group consisting of genus *Heterosigma*, and *Chattonella*.

13. The composition of claim 11, wherein the raphidophyte is selected from the group consisting of species *Heterosigma akashiwo*, and *Chattonella subsalsa*.

14. A method for reducing nitric oxide, comprising applying an effective amount of a fusion protein, wherein the fusion protein comprises a nitrate reductase (NR) and a truncated hemoglobin N (trHbN) domain, and wherein the fusion protein comprises a polypeptide having an amino acid sequence at least 90% identical to SEQ ID NO: 3 or 5.

15. The method of claim 14, wherein the fusion protein converts nitric oxide to nitrate and nitrite.

16. The method of claim 14, wherein the fusion protein comprises a polypeptide having the amino acid sequence of SEQ ID NO: 3 or 5.

17. The method of claim 14, wherein the fusion protein is derived from a raphidophyte.

18. The method of claim 17, wherein the raphidophyte is selected from the group consisting of genus *Heterosigma*, and *Chattonella*.

19. The method of claim 17, wherein the raphidophyte is selected from the group consisting of species *Heterosigma akashiwo*, and *Chattonella subsalsa*.

20. The method of claim 14, wherein the fusion protein reduces nitric oxide by at least 50%.

\* \* \* \* \*

SEQUENCE LISTING

```
<160> NUMBER OF SEQ ID NOS: 13

<210> SEQ ID NO 1
<211> LENGTH: 3019
<212> TYPE: DNA
<213> ORGANISM: Heterosigma akashiwo
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t

<400> SEQUENCE: 1
aagcttagaa ggagatatac atatggcccc tccttctacg atcaagattg gcgggtacac      60
ttgccctaag gttgacatca gagaggttga tcctcgggac gaaaagaccc ccgatgactg     120
gatccctcgc caccctgact tggtcagact gacaggtcgc cacccctcca actgcgagcc     180
tccggtcatg gacctgatga gccatggctt catcacccc acgtccttgc actacgtacg      240
caaccacggt gcggctccaa atctcgattg ggactcccat cgtgtcagaa tctcaggcct     300
ggtagacaaa cccatggaac tatcgatggc tgacttcacc gacccccacca agttcgagca    360 ggtatctatt cctgtgaccc tcgtgtgtgc tggaaaccgg cgcaaggagc agaactcggt    420
aaagcagggc attggcttca actgggggcn agcggccgtg tctactagcg tatggactgg    480
gggtgagggt gagggatgta cttgaatact gnggattgaa atcacaggat gagggtgcca    540
atcatgtgtg ctttgttggt gcagaccctc ttcctggtgg gtactacggg accagcatca    600
tacgccatgt gagtacctta ccaggtttac ttgagtatga gtgtaccagt gcacctctct    660
acacaaatga acttccatgc atagttaacc tcctcttaac actacagcat ggtgaactgc    720
ttctaacata tgtagctttt caacaacttg atttgtggcc taaatgtctt gccttgcact    780
gttttctcag gctgccatgg acccegcectc tgacgtcatg ctgtgctggg agcagaacgg    840
```

```
cgagcgcctg acccctgacc acggctatcc catccggctg atcatcccag gctacattgg      900
tggtcgcatg gtcaagtggc tgacagacat ctctgtcact gaagttgagt ctgacaatca      960
ctaccactat catgacaata gagtcctgcc ccctcagatt gatgctgaca ccgccaaggc     1020
agatggctgg tggtacaagc cagaatacat catcaatgac ctgaacatca attctgctat     1080
cacctcacca gctcatgacg aggtcgtgac catcatccct gggcagaaag caacttacgc     1140
ctgcaagggg tacgcctact caggtggtgg gcgcaaggtg actcgtgtgg agctgagctt     1200
cgatgagggt gagacttggg agctgaccac actgacgcac ccggagcggc caacacgggc     1260
gggcaagcac tggtgctggt gcttctggga gtatgaggtg cccatcatgc gcatgctgcg     1320
ggccaagcag atgatggtgc gtgcctggga cactggcctc aacacgcagc ccatgaactt     1380
cacctggaat gtgatgggca tgatgaacaa ctgcacattc aaggtgcgca tccacgacgc     1440
cagcgagggc aatggtcttt ccctgaagtt tgagcacccc acccagcctg gtgtgctgcc     1500
aggaggctgg atggtgccca agtggaggt gcaggcggcg gtgcaggtgg agaagaaagt     1560
ggaggctaag gctggtgtga agtacttcac agaggaggag gtggccaagc acactgagcg     1620
ggacgatgcg tggtttatct acgatggcaa ggtgtatgat gcaactccgt tcatggacga     1680
tcaccccggc ggcgcagact ccattcttct gacagcaggc gaggacgcca ctgaggagtt     1740
tgactccctg cattccgaga aggcgaagaa gatgctggat gactactaca ttggtgagct     1800
gggtacagca cctgcagcga gtgccccccc ccctcctgct gtgagcctgt tgagaagct     1860
gggtgggggt gaagcagtca atgctgtggt gaataagttc tacgatgaaa aggtgctgaa     1920
ggataccagc ctatccccaa tcttcgatgg caaagatgtt gagtccttga aaatgcatca     1980
gggtatgttc cttcagtggg cacttggggg ggagaacggc tacaccgggc ggtccatgaa     2040
ggaggcccac gctggtttgg gcatcactga ggcccactgg aacacggtgt gtgggcacct     2100
ggtgggcaca ctgcaggagc tgggtgtgtc ggcggcagac atcgacacag tggtgtccaa     2160
ggtggcgccc ctgaaggacg acattgtggg gacttcggcg ctgaaccgac ccaaggcgct     2220
gaacaagaag aagaagatgg cgtttgcgct ggtggagcgg gaggagatca cacacaatgt     2280
gcggcggcta cggtttgcgc tgcagtcccc ggagcatgtt ctgggcttgc cagtgggcca     2340
gcacatgttt gtctcggcca agatcgatgg tgctcttgc atgcgcgcct acacaccact     2400
cacaggtgac gaggtccagg ggtactttga tctgctgatc aaggtgtact atgcaaatga     2460
gcaccccaag ttcccggagg gtggcaagat gagccagcac ctgaacagct tgaccattgg     2520
tcagaccatt gacgtgcgcg gccctctcgg ccacattgac tacaagggca agggttttgtt     2580
tgatattgac ggcaaggaga tccagtgtcg ggacatcctg atgatggcag ggggcacagg     2640
catcaccccc atgtggcaag taatgtctgc tgttcttcgg gatgaggcag attccaccaa     2700
gctgaacctg atctttgcca acaacacaga ggatgacatc ctcctgcagg aagagctgaa     2760
tgatatggac tcagagaacg agcaatgcca ggtataccac acaatagcca ccccaaagaa     2820
ccctgagaca tggtctcaag gagtgggctt catcacacag gagatggtgg agcagcagtt     2880
tggtccggct cgcgacgatg cgattgtgtt cctgtgcggg cctccccta tgattaactt     2940
tgcttgttta ccagccctgg aggctctggg ttacaagaag gagcagattt tcagttttta     3000
gtgaattcga gcaagctta                                                  3019
```

<210> SEQ ID NO 2
<211> LENGTH: 2869
<212> TYPE: DNA
<213> ORGANISM: Heterosigma akashiwo

```
<400> SEQUENCE: 2 attcccttc   ttttagtctg   accaattgag   acaaagatgg   cccctccttc   tacgatcaag     60
attggcgggt  acacttgccc   tagggttgac   atcagagagg   ttgatcctcg   ggacgaaaag    120 accccgatg   actggatccc   tcgccaccct   gacttggtca   gactgacagg   tcgccacccc    180
ttcaactgcg  agcctccggt   catgacctg    atgagccatg   gcttcatcac   ccccacgtcc    240
ttgcactacg  tacgcaacca   cggtgcggct   ccaaatctcg   attgggactc   ccatcgtgtc    300
agaatctcag  gcctggtaga   caaacccatg   gaactatcga   tggctgactt   caccgacccc    360
accaagttcg  agcaggtgtc   tattcctgtg   accctcgtgt   gtgctggaaa   ccggcgcaag    420
gagcagaact  cggtaaagca   gggcattggc   ttcaactggg   ggccagcggc   cgtgtctact    480
agcgtatgga  ctggggtgag   ggtgagggat   gtacttgaat   actgtggatt   gaaatcacag    540
gatgagggtg  ccaatcatgt   gtgctttgtt   ggtgcagacc   ctcttcctgg   tgggtactac    600
gggaccagca  tcatacgcca   tgctgccatg   gaccccgcct   ctgacgtcat   gctgtgctgg    660
gagcagaacg  gcgagcgcct   gaccctgac   acggctatc    ccatccggct   gatcatccca    720
ggctacattg  tggtcgcat    gatcaagtgg   ctgacagaca   tctctgtcac   tgaagttgag    780
tctgacaatc  actaccacta   tcatgacaac   agagtcctgc   cccctcagat   tgatgctgac    840
accgccaagg  cagatggctg   gtggtacaag   ccagaataca   tcatcaatga   cctgaacatc    900
aactctgcca  tcacctcacc   agctcatgac   gaggtcgtga   ccatcatccc   tgggcagaaa    960
gcaacttacg  cctgcaaggg   gtacgcctac   tcaggtggtg   ggcgcaaggt   gactcgtgtg   1020
gagctgagct  tcgatgaggg   tgagacttgg   gagctgacca   cactgacaca   cccggagcgg   1080
cctacacggg  cgggcaagca   ctggtgctgg   tgcttctggg   agtatgaggt   gcccatcatg   1140
cgcatgctgc  gggccaagca   gatgatggtg   cgtgcctggg   acactggcct   caacacgcag   1200
cccatgaact  tcacctggaa   tgtgatgggt   atgatgaaca   actgcacatt   caaggtgcgc   1260
atccacgacg  ccagcgaggg   caatggtctt   tccctgaagt   ttgagcaccc   cacccagcct   1320
ggtgtgctcc  caggaggctg   gatggtgccc   aaggtggagg   tgcaggcggc   ggtgcaggtg   1380
gagaagaaag  tggaggctaa   ggctggtgtg   aagtacttca   cagaggagga   ggtggccaag   1440
cacactgagc  gggacgatgc   gtggtttatc   tacgatggca   aggtgtatga   tgcaacgccg   1500
ttcatggacg  atcaccccag   cggcgcagac   tccattcttc   tgacagcagg   cgaggacgcc   1560
actgaggagt  ttgactccct   acattccgag   aaggcgaaga   agatgctgga   tgactactac   1620
attggtgagc  tgggtacagc   acctgcagcg   agtgcccccc   cccctcctgc   tgtgagcctg   1680
tttgagaagc  tgggtggggg   tgaagcagtc   aatgctgtgg   tgaataagtt   ctacgatgaa   1740
aaggtgctga  aggataccag   cctatcccca   atcttcgatg   gcaaagatgt   tgagtccttg   1800
aaaatgcatc  agcgtatgtt   ccttcagtgg   gtacttgggg   gggaaaacgg   ctacaccggg   1860
cggtccatga  aggaggccca   cgctggtttg   ggcatcactg   aggcccactg   gaacacggtg   1920
tgtgggcacc  tggtgggcac   actgcaggag   ctgggtgtgt   cggcggcaga   catcgacaca   1980
gtggtgtcca  aggtggcgcc   cctgaaggac   gacgttgtgg   ggacttcagc   gctgaaccga   2040
cccaaggcgc  tgaacaagaa   gaagaagatg   gcgtttgcgc   tggtggagcg   ggaggagatc   2100
acacacaatg  tgcggcggct   acggtttgcg   ctgcagtccc   cggagcatgt   tctgggcttg   2160
ccagtgggcc  agcacatgtt   tgtctcggcc   aagatcgatg   gtgctctttg   catgcgcgcc   2220
tacacaccac  tcacaggtga   cgaggtccag   gggtactttg   acctgctgat   caaggtgtac   2280
tatgcaaatg  agcaccccaa   gttcccggag   ggtggcaaga   tgagccagca   cctgaacagc   2340
```

-continued

```
ttgaccattg gtcagaccat tgatgtgcgc ggccctctcg gccacattga ctacaagggc    2400
aagggtttgt ttgatattga cggcaaggag atccagtgtc gggacatcct gatgatggca    2460
gggggcacag gcatcacccc catgtggcaa gtaatgtctg ctgttcttcg ggatgaggca    2520
gattccacca aactgaacct gatctttgcc aacaacacag aggatgacat cctcctgcag    2580
gaagagctga atgatatgga ctcagagaac gagcaatgcc aggtatacca cacaatagcc    2640
accccaaaga accctgagac atggtctcaa ggagtgggct tcatcacaca ggagatggtg    2700
gagcagcagt ttggtccggc tcgcgacgat gcgattgtgt tcctgtgcgg gcctcccccct   2760 atgattaact ttgcttgttt gccagccctg gaggctctgg gttacaagaa ggagcagatt    2820
tttcagtttt agtcaagccc tgatgtattt aaaaattata ataataatg                2869
```

<210> SEQ ID NO 3
<211> LENGTH: 931
<212> TYPE: PRT
<213> ORGANISM: Heterosigma akashiwo

<400> SEQUENCE: 3

```
Met Ala Pro Pro Ser Thr Ile Lys Ile Gly Gly Tyr Thr Cys Pro Arg
  1               5                  10                  15

Val Asp Ile Arg Glu Val Asp Pro Arg Asp Glu Lys Thr Pro Asp Asp
             20                  25                  30

Trp Ile Pro Arg His Pro Asp Leu Val Arg Leu Thr Gly Arg His Pro
         35                  40                  45

Phe Asn Cys Glu Pro Pro Val Met Asp Leu Met Ser His Gly Phe Ile
     50                  55                  60

Thr Pro Thr Ser Leu His Tyr Val Arg Asn His Gly Ala Ala Pro Asn
 65                  70                  75                  80

Leu Asp Trp Asp Ser His Arg Val Arg Ile Ser Gly Leu Val Asp Lys
                 85                  90                  95

Pro Met Glu Leu Ser Met Ala Asp Phe Thr Asp Pro Thr Lys Phe Glu
            100                 105                 110

Gln Val Ser Ile Pro Val Thr Leu Val Cys Ala Gly Asn Arg Arg Lys
        115                 120                 125

Glu Gln Asn Ser Val Lys Gln Gly Ile Gly Phe Asn Trp Gly Pro Ala
    130                 135                 140

Ala Val Ser Thr Ser Val Trp Thr Gly Val Arg Val Arg Asp Val Leu
145                 150                 155                 160

Glu Tyr Cys Gly Leu Lys Ser Gln Asp Glu Gly Ala Asn His Val Cys
                165                 170                 175

Phe Val Gly Ala Asp Pro Leu Pro Gly Gly Tyr Tyr Gly Thr Ser Ile
            180                 185                 190

Ile Arg His Ala Ala Met Asp Pro Ala Ser Asp Val Met Leu Cys Trp
        195                 200                 205

Glu Gln Asn Gly Glu Arg Leu Thr Pro Asp His Gly Tyr Pro Ile Arg
    210                 215                 220

Leu Ile Ile Pro Gly Tyr Ile Gly Gly Arg Met Ile Lys Trp Leu Thr
225                 230                 235                 240

Asp Ile Ser Val Thr Glu Val Glu Ser Asp Asn His Tyr His Tyr His
                245                 250                 255

Asp Asn Arg Val Leu Pro Pro Gln Ile Asp Ala Asp Thr Ala Lys Ala
            260                 265                 270

Asp Gly Trp Trp Tyr Lys Pro Glu Tyr Ile Ile Asn Asp Leu Asn Ile
        275                 280                 285
```

```
Asn Ser Ala Ile Thr Ser Pro Ala His Asp Glu Val Val Thr Ile Ile
    290                 295                 300

Pro Gly Gln Lys Ala Thr Tyr Ala Cys Lys Gly Tyr Ala Tyr Ser Gly
305                 310                 315                 320

Gly Gly Arg Lys Val Thr Arg Val Glu Leu Ser Phe Asp Glu Gly Glu
                325                 330                 335

Thr Trp Glu Leu Thr Thr Leu Thr His Pro Glu Arg Pro Thr Arg Ala
            340                 345                 350

Gly Lys His Trp Cys Trp Cys Phe Trp Glu Tyr Glu Val Pro Ile Met
        355                 360                 365

Arg Met Leu Arg Ala Lys Gln Met Met Val Arg Ala Trp Asp Thr Gly
    370                 375                 380

Leu Asn Thr Gln Pro Met Asn Phe Thr Trp Asn Val Met Gly Met Met
385                 390                 395                 400

Asn Asn Cys Thr Phe Lys Val Arg Ile His Asp Ala Ser Glu Gly Asn
                405                 410                 415

Gly Leu Ser Leu Lys Phe Glu His Pro Thr Gln Pro Gly Val Leu Pro
            420                 425                 430

Gly Gly Trp Met Val Pro Lys Val Glu Val Gln Ala Ala Val Gln Val
        435                 440                 445

Glu Lys Lys Val Glu Ala Lys Ala Gly Val Lys Tyr Phe Thr Glu Glu
    450                 455                 460

Glu Val Ala Lys His Thr Glu Arg Asp Asp Ala Trp Phe Ile Tyr Asp
465                 470                 475                 480

Gly Lys Val Tyr Asp Ala Thr Pro Phe Met Asp Asp His Pro Ser Gly
                485                 490                 495

Ala Asp Ser Ile Leu Leu Thr Ala Gly Glu Asp Ala Thr Glu Glu Phe
            500                 505                 510

Asp Ser Leu His Ser Glu Lys Ala Lys Lys Met Leu Asp Asp Tyr Tyr
        515                 520                 525

Ile Gly Glu Leu Gly Thr Ala Pro Ala Ala Ser Ala Pro Pro Pro Pro
    530                 535                 540

Ala Val Ser Leu Phe Glu Lys Leu Gly Gly Gly Glu Ala Val Asn Ala
545                 550                 555                 560

Val Val Asn Lys Phe Tyr Asp Glu Lys Val Leu Lys Asp Thr Ser Leu
                565                 570                 575

Ser Pro Ile Phe Asp Gly Lys Asp Val Glu Ser Leu Lys Met His Gln
            580                 585                 590

Arg Met Phe Leu Gln Trp Val Leu Gly Gly Glu Asn Gly Tyr Thr Gly
        595                 600                 605

Arg Ser Met Lys Glu Ala His Ala Gly Leu Gly Ile Thr Glu Ala His
    610                 615                 620

Trp Asn Thr Val Cys Gly His Leu Val Gly Thr Leu Gln Glu Leu Gly
625                 630                 635                 640

Val Ser Ala Ala Asp Ile Asp Thr Val Ser Lys Val Ala Pro Leu
                645                 650                 655

Lys Asp Asp Val Val Gly Thr Ser Ala Leu Asn Arg Pro Lys Ala Leu
            660                 665                 670

Asn Lys Lys Lys Met Ala Phe Ala Leu Val Glu Arg Glu Ile
        675                 680                 685

Thr His Asn Val Arg Arg Leu Arg Phe Ala Leu Gln Ser Pro Glu His
    690                 695                 700

Val Leu Gly Leu Pro Val Gly Gln His Met Phe Val Ser Ala Lys Ile
```

-continued 705 710 715 720

Asp Gly Ala Leu Cys Met Arg Ala Tyr Thr Pro Leu Thr Gly Asp Glu
725 730 735

Val Gln Gly Tyr Phe Asp Leu Leu Ile Lys Val Tyr Tyr Ala Asn Glu
740 745 750

His Pro Lys Phe Pro Glu Gly Gly Lys Met Ser Gln His Leu Asn Ser
755 760 765

Leu Thr Ile Gly Gln Thr Ile Asp Val Arg Gly Pro Leu Gly His Ile
770 775 780

Asp Tyr Lys Gly Lys Gly Leu Phe Asp Ile Asp Gly Lys Glu Ile Gln
785 790 795 800

Cys Arg Asp Ile Leu Met Met Ala Gly Gly Thr Gly Ile Thr Pro Met
805 810 815

Trp Gln Val Met Ser Ala Val Leu Arg Asp Glu Ala Asp Ser Thr Lys
820 825 830

Leu Asn Leu Ile Phe Ala Asn Asn Thr Glu Asp Asp Ile Leu Leu Gln
835 840 845

Glu Glu Leu Asn Asp Met Asp Ser Glu Asn Glu Gln Cys Gln Val Tyr
850 855 860

His Thr Ile Ala Thr Pro Lys Asn Pro Glu Thr Trp Ser Gln Gly Val
865 870 875 880

Gly Phe Ile Thr Gln Glu Met Val Glu Gln Gln Phe Gly Pro Ala Arg
885 890 895

Asp Asp Ala Ile Val Phe Leu Cys Gly Pro Pro Pro Met Ile Asn Phe
900 905 910

Ala Cys Leu Pro Ala Leu Glu Ala Leu Gly Tyr Lys Lys Glu Gln Ile
915 920 925

Phe Gln Phe
930

<210> SEQ ID NO 4
<211> LENGTH: 2025
<212> TYPE: DNA
<213> ORGANISM: Chattonella subsalsa

<400> SEQUENCE: 4
ggatgattaa atggctgaca gatattgaag tgacttccga acagtcctcg aatcactacc 60
actatcacga caaccgagtg cttcctccac aaattgatgc agaaagagca ttagcggaga 120
agtggtggta caagcctgag tatataataa atgatttgaa cattaattca gccattactt 180
ccccagcaca cggcgaagaa ttggtactat catcatcgaa ccaacaaasa tacaaatgca 240
aagggtacgc atattctggt ggaggaaggc aagttactcg agtggagctt tcttttgatg 300
atggggaaac gtgggatctt tgcacattga accacccaga aaagccaacc aaagctggta 360
aatattggtg ttggtgcttt tgggaatatg atgtatctat cctgaagcta gttcgtagca 420
agcaaatgat ggttcgggca tgggacacgg gtcttaacac tcaaccaatg aattttacat 480
ggaatgtcat gggcatgatg aacaacagca ctttcaaggt caaaattgat gctcgtacaa 540
cccaaaccgc tgagtcttta aagttttcat tagcttttga acacccaaca caaccaggag 600
cwttgccagg aggttggatg gtacccaaaa ttgagtcccr acaaacagag cacaagaagg 660
ctgaaacaaa agatgtgggc aaagggaaca ggaagcygta tcctttggaa gaagttgcaa 720
aacacactac aaaggaagac tgctggtttg tatatgatgg caaagttttt gacagtacaa 780
gcttcatgga tgatcatcct ggtggtgctg atagcatact ccttactgcc ggagaagatg 840

-continued

```
caacagaaga rtttgattct ttgcactcag agaaagcycg caaaatgctt gataactatt    900
acattggaga tcttgcctca gaagatgcag tagaggtgca aaggaatgca ttgcctggaa    960
raaagagtrg ccaagtgagc ttgtatgaga agttgggggg tgaagctgca atccaagctg   1020
tagttgagaa attttacgaa gaaaagttt tgaaagacaa cctgctgagt ccaatctttg    1080
agtctcgtga cattaagtct ttgaaacttc accagaaact atttctcaag tatgctctgg   1140
gtgggacaaa agcctacgat ggaaggtcga tgtcagatgc tcaccgtgga ttgggaatca   1200
aagaacctca ttggaaagct gtgtgtggac actyggtgaa cacgttgact gagttgggtg   1260
tttctcgtga acatatagat gaagtagtgc agagagtcct ccctctccat gatgatattg   1320
ttgaarcacc ctcttctgaa ktagtagaat ccaacccaat tgcattggat aggaaaaaga   1380
agaatgcttt tgccttgtta gaaaaagttc aagtaagcca caacaccatc aagcttagat   1440
ttgctcttcc aactgatgat cacatcctag gtctgcccgt tggraaacac atgttcatca   1500
gtgcaaagat caatggatct atgtgcatgc gagcatacac tccaatcaca ggrgatgaag   1560
tcaagggtca ctttgatctt gtcatcaaag tttacttcaa aaatgagcac cccaaattcc   1620
ctgagggtgg gaagatgtcg caatacctta atgagttaca acttggacaa acaattgacg   1680
tcagaggccc actgggacat atcaactacc ttgggaaagg agaattyaac atcgatggta   1740 cctcaattt r tgyttctaac attgtcatga tggcaggtgg aacaggratt actccaatgt   1800
ttcaagttat ttctgcaatc ttacgggatg ctgaagattt cacaaatgtt ttcttgatat   1860
atgcaaacaa tactgaagat gatatcctyt tgctggagga gttagatcaa atgtccaaaa   1920
gtcaaaactg ctcgatattc cataccttag caacacccma aaattcagag gtttggaaag   1980
gaggggtggg atttattaca gaagacatgg tcaaacagaa tttcc                   2025
```

```
<210> SEQ ID NO 5
<211> LENGTH: 674
<212> TYPE: PRT
<213> ORGANISM: Chattonella subsalsa
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (320)..(320)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (442)..(442)
<223> OTHER INFORMATION: Xaa can be any naturally occurring amino acid
<220> FEATURE:
<221> NAME/KEY: misc_feature
<222> LOCATION: (447)..(447)
<223> OTHER INFORMATION: Xaa can be any naturally occurring amino acid
<220> FEATURE:
<221> NAME/KEY: misc_feature
<222> LOCATION: (583)..(584)
```

```
<223> OTHER INFORMATION: Xaa can be any naturally occurring amino acid
<220> FEATURE:
<221> NAME/KEY: misc_feature
<222> LOCATION: (653)..(653)
<223> OTHER INFORMATION: Xaa can be any naturally occurring amino acid

<400> SEQUENCE: 5
```

Met Ile Lys Trp Leu Thr Asp Ile Glu Val Thr Ser Glu Gln Ser Ser
1               5                   10                  15

Asn His Tyr His Tyr His Asp Asn Arg Val Leu Pro Pro Gln Ile Asp
            20                  25                  30

Ala Glu Arg Ala Leu Ala Glu Lys Trp Trp Tyr Lys Pro Glu Tyr Ile
        35                  40                  45

Ile Asn Asp Leu Asn Ile Asn Ser Ala Ile Thr Ser Pro Ala His Gly
    50                  55                  60

Glu Glu Leu Val Leu Ser Ser Ser Asn Gln Gln Xaa Tyr Lys Cys Lys
65                  70                  75                  80

Gly Tyr Ala Tyr Ser Gly Gly Gly Arg Gln Val Thr Arg Val Glu Leu
                85                  90                  95

Ser Phe Asp Asp Gly Glu Thr Trp Asp Leu Cys Thr Leu Asn His Pro
            100                 105                 110

Glu Lys Pro Thr Lys Ala Gly Lys Tyr Trp Cys Trp Cys Phe Trp Glu
        115                 120                 125

Tyr Asp Val Ser Ile Leu Lys Leu Val Arg Ser Lys Gln Met Met Val
    130                 135                 140

Arg Ala Trp Asp Thr Gly Leu Asn Thr Gln Pro Met Asn Phe Thr Trp
145                 150                 155                 160

Asn Val Met Gly Met Met Asn Asn Ser Thr Phe Lys Val Lys Ile Asp
                165                 170                 175

Ala Arg Thr Thr Gln Thr Ala Glu Ser Leu Lys Phe Ser Leu Ala Phe
            180                 185                 190

Glu His Pro Thr Gln Pro Gly Ala Leu Pro Gly Gly Trp Met Val Pro
        195                 200                 205

Lys Ile Glu Ser Xaa Gln Thr Glu His Lys Lys Ala Glu Thr Lys Asp
    210                 215                 220

Val Gly Lys Gly Asn Arg Lys Xaa Tyr Pro Leu Glu Glu Val Ala Lys
225                 230                 235                 240

His Thr Thr Lys Glu Asp Cys Trp Phe Val Tyr Asp Gly Lys Val Phe
                245                 250                 255

Asp Ser Thr Ser Phe Met Asp Asp His Pro Gly Gly Ala Asp Ser Ile
            260                 265                 270

Leu Leu Thr Ala Gly Glu Asp Ala Thr Glu Glu Phe Asp Ser Leu His
        275                 280                 285

Ser Glu Lys Ala Arg Lys Met Leu Asp Asn Tyr Tyr Ile Gly Asp Leu
    290                 295                 300

Ala Ser Glu Asp Ala Val Glu Val Gln Arg Asn Ala Leu Pro Gly Xaa
305                 310                 315                 320

Lys Ser Xaa Gln Val Ser Leu Tyr Glu Lys Val Gly Gly Glu Ala Ala
                325                 330                 335

Ile Gln Ala Val Val Glu Lys Phe Tyr Glu Glu Lys Val Leu Lys Asp
            340                 345                 350

Asn Leu Leu Ser Pro Ile Phe Glu Ser Arg Asp Ile Lys Ser Leu Lys
        355                 360                 365

Leu His Gln Lys Leu Phe Leu Lys Tyr Ala Leu Gly Gly Thr Lys Ala
    370                 375                 380

Tyr Asp Gly Arg Ser Met Ser Asp Ala His Arg Gly Leu Gly Ile Lys
385                 390                 395                 400

Glu Pro His Trp Lys Ala Val Cys Gly His Xaa Val Asn Thr Leu Thr
            405                 410                 415

Glu Leu Gly Val Ser Arg Glu His Ile Asp Glu Val Val Gln Arg Val
        420                 425                 430

Leu Pro Leu His Asp Asp Ile Val Glu Xaa Pro Ser Ser Glu Xaa Val
    435                 440                 445

Glu Ser Asn Pro Ile Ala Leu Asp Arg Lys Lys Asn Ala Phe Ala
450                 455                 460

Leu Leu Glu Lys Val Gln Val Ser His Asn Thr Ile Lys Leu Arg Phe
465                 470                 475                 480

Ala Leu Pro Thr Asp Asp His Ile Leu Gly Leu Pro Val Gly Lys His
            485                 490                 495

Met Phe Ile Ser Ala Lys Ile Asn Gly Ser Met Cys Met Arg Ala Tyr
                500                 505                 510

Thr Pro Ile Thr Gly Asp Glu Val Lys Gly His Phe Asp Leu Val Ile
        515                 520                 525

Lys Val Tyr Phe Lys Asn Glu His Pro Lys Pro Glu Gly Gly Lys
    530                 535                 540

Met Ser Gln Tyr Leu Asn Glu Leu Gln Leu Gly Gln Thr Ile Asp Val
545                 550                 555                 560

Arg Gly Pro Leu Gly His Ile Asn Tyr Leu Gly Lys Gly Glu Phe Asn
            565                 570                 575

Ile Asp Gly Thr Ser Ile Xaa Xaa Ser Asn Ile Cys Met Met Ala Gly
                580                 585                 590

Gly Thr Gly Ile Thr Pro Met Phe Gln Val Ile Ser Ala Ile Leu Arg
        595                 600                 605

Asp Ala Glu Asp Phe Thr Asn Val Phe Leu Ile Tyr Ala Asn Asn Thr
    610                 615                 620

Glu Asp Asp Ile Leu Leu Leu Glu Glu Leu Asp Gln Met Ser Lys Ser
625                 630                 635                 640

Gln Asn Cys Ser Ile Phe His Thr Leu Ala Thr Pro Xaa Asn Ser Glu
            645                 650                 655

Val Trp Lys Gly Gly Val Gly Phe Ile Thr Glu Asp Met Val Lys Gln
                660                 665                 670

Asn Phe

<210> SEQ ID NO 6
<211> LENGTH: 19
<212> TYPE: DNA
<213> ORGANISM: Artificial Sequence
<220> FEATURE:
<223> OTHER INFORMATION: synthetic

<400> SEQUENCE: 6
aagcccagaa catgctccg                                              19

<210> SEQ ID NO 7
<211> LENGTH: 20
<212> TYPE: DNA
<213> ORGANISM: Artificial Sequence
<220> FEATURE:
<223> OTHER INFORMATION: synthetic

<400> SEQUENCE: 7
gctggtatcc ttcagcacct                                             20

<210> SEQ ID NO 8
<211> LENGTH: 50
<212> TYPE: DNA
<213> ORGANISM: Artificial Sequence
<220> FEATURE:
<223> OTHER INFORMATION: synthetic

<400> SEQUENCE: 8
aagcttagaa ggagatatac atatggcccc tccttctacg atcaagattg            50

<210> SEQ ID NO 9
<211> LENGTH: 45
<212> TYPE: DNA
<213> ORGANISM: Artificial Sequence
<220> FEATURE:
<223> OTHER INFORMATION: synthetic

<400> SEQUENCE: 9
aagcttgctc gaattcacta aaactgaaaa atctgctcct tcttg                 45

<210> SEQ ID NO 10
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 10
athggnggnm gnatgathaa rtgg                                        24

<210> SEQ ID NO 11
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: n is a, c, g, or t

<400> SEQUENCE: 11
rttrttcatc atncccat                                               18

<210> SEQ ID NO 12
<211> LENGTH: 20
<212> TYPE: DNA
<213> ORGANISM: Artificial Sequence
<220> FEATURE:
<223> OTHER INFORMATION: synthetic

<400> SEQUENCE: 12
ttccgaacag tcctcgaatc                                             20

<210> SEQ ID NO 13
<211> LENGTH: 20
<212> TYPE: DNA

-continued

```
<213> ORGANISM: Artificial Sequence
<220> FEATURE:
<223> OTHER INFORMATION: synthetic

<400> SEQUENCE: 13
ctgtgagcct gtttgagaag                                             20
```